United States Patent
Durand et al.

(10) Patent No.: US 7,655,251 B2
(45) Date of Patent: Feb. 2, 2010

(54) AMPHIPHILIC DERIVATIVES OF α-C-PHENYL-N-TERT-BUTYLNITRONE

(75) Inventors: Grégory Durand, Villeneuve les Avignon Cedex (FR); Ange Polidori, Avignon (FR); Bernard Pucci, Molleges (FR)

(73) Assignees: TS Pharma (FR); Universite d'Avignon Et des Pays du Vaucluse (FR)

( * ) Notice: Subject to any disclaimer, the term of this patent is extended or adjusted under 35 U.S.C. 154(b) by 574 days.

(21) Appl. No.: 10/533,982

(22) PCT Filed: Nov. 7, 2003

(86) PCT No.: PCT/FR03/03335

§ 371 (c)(1),
(2), (4) Date: Oct. 24, 2005

(87) PCT Pub. No.: WO2004/043982

PCT Pub. Date: May 27, 2004

(65) Prior Publication Data

US 2006/0120985 A1 Jun. 8, 2006

(30) Foreign Application Priority Data

Nov. 8, 2002 (FR) .................................. 02 14078

(51) Int. Cl.
*A61K 8/02* (2006.01)
*A61K 31/70* (2006.01)
*A61K 31/74* (2006.01)
*C07H 15/00* (2006.01)

(52) U.S. Cl. .................... 424/401; 424/78.31; 536/17.9
(58) Field of Classification Search ................. 536/17.9
See application file for complete search history.

(56) References Cited

U.S. PATENT DOCUMENTS 5,455,272 A  10/1995  Janzen et al.

FOREIGN PATENT DOCUMENTS

WO   WO 91/05552 A   5/1991

OTHER PUBLICATIONS

O. Ouari et al., "Synthesis of a glycolipidic amphilic nitrone as a new spin trap", *J. Org. Chem.*, vol. 64, 1999, pp. 3554-3556.

Floyd R.A. et al., "Protection against oxidative damage to CNS by alpha-phenyl-tert-butyl nitrone and other spin-trapping agents: a novel series of nonlipid free radical scavengers", Emerging Strategies in Neuroprotection, 1992, pp. 252-272.

S. Tanguy, et al.; "Protection Against Reactive Oxygen Species Injuries in Rat Isolated Perfused Hearts: Effects of LPBNAH, a New Amphiphilic Spin-Trap Derived from PBN"; Cardiovascular Drugs and Therapy, vol. 20; pp. 147-149; Published Online Mar. 9, 2006.

B. Poeggeler, et al.; "Mitochondrial Medicine: Neuroprotection and Life Extension by the New Amphiphilic Nitrone LPBNAH[1] Acting as a Highly Potent Antioxidant Agent"; Journal of Neurochemistry, 2005, 95; pp. 962-973.

T. Asanuma, et al.; "A New Amphiphilic Derivative, N-{[4-(Lactobionamido)methyl]benzylidene}-1,1-dimethyl-2-(octylsulfanyl)ethylamine N-Oxide, Has a Protective Effect Against Copper-Induced Fulminant Hepatitis in Long-Evans Cinnamon Rats at an Extremely Low Concentration Compared with its Original Form α-Phenyl-N-(tert-butyl) Nitrone"; Chemistry & Biodiversity; vol. 4, 2007; pp. 2253-2267.

*Primary Examiner*—Elli Peselev
(74) *Attorney, Agent, or Firm*—Alston & Bird LLP

(57) ABSTRACT

Novel compounds, derivatives of α-C-phenyl N-tert-butyl nitrone, a method for production and use thereof for the preparation of medicaments for the prevention of treatment of diseases related to oxidative stress.

12 Claims, 13 Drawing Sheets

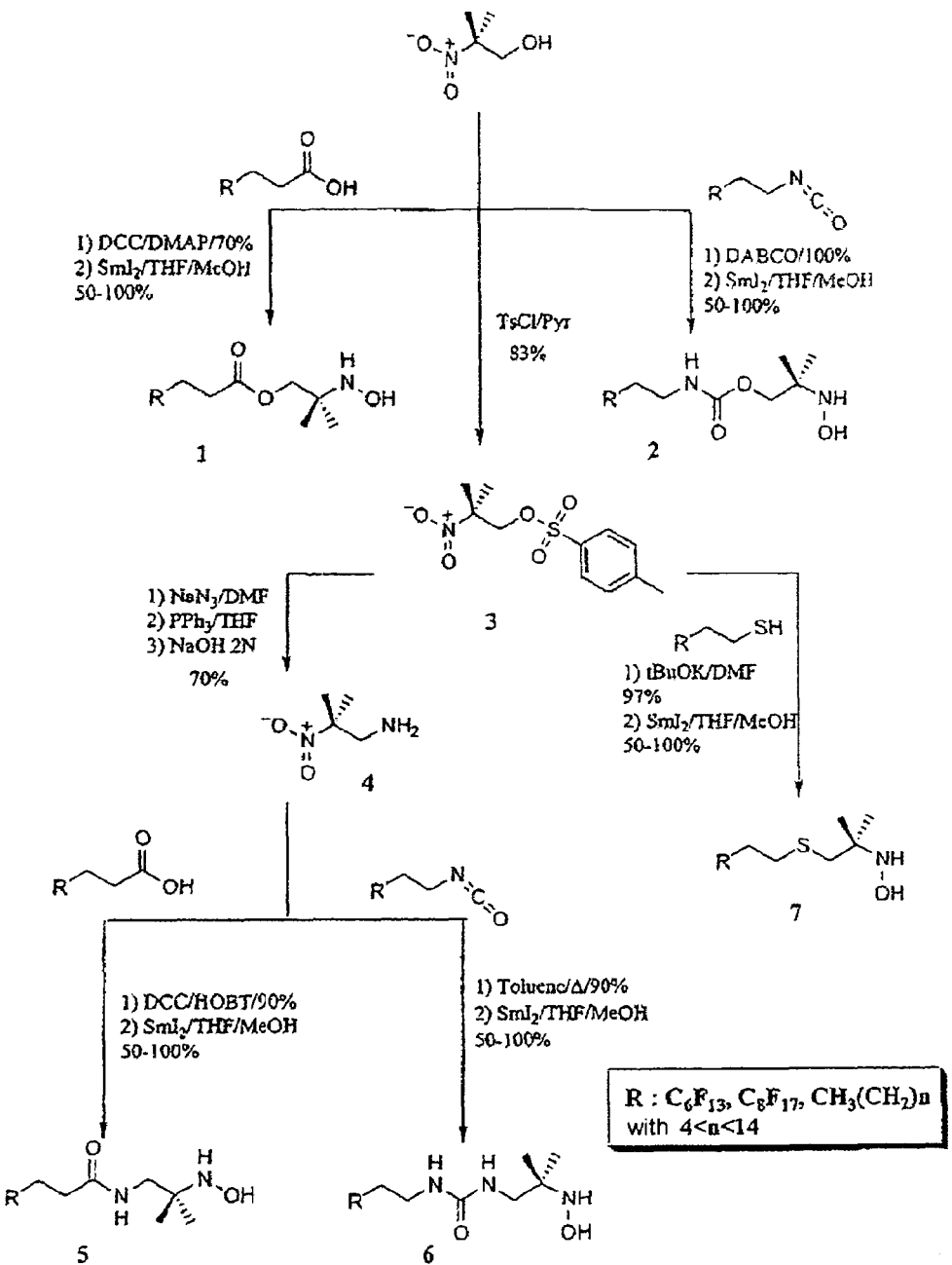
Figure 1: Synthesizing the hydrophobic monocatenary hydrocarbon and perfluorocarbon moieties

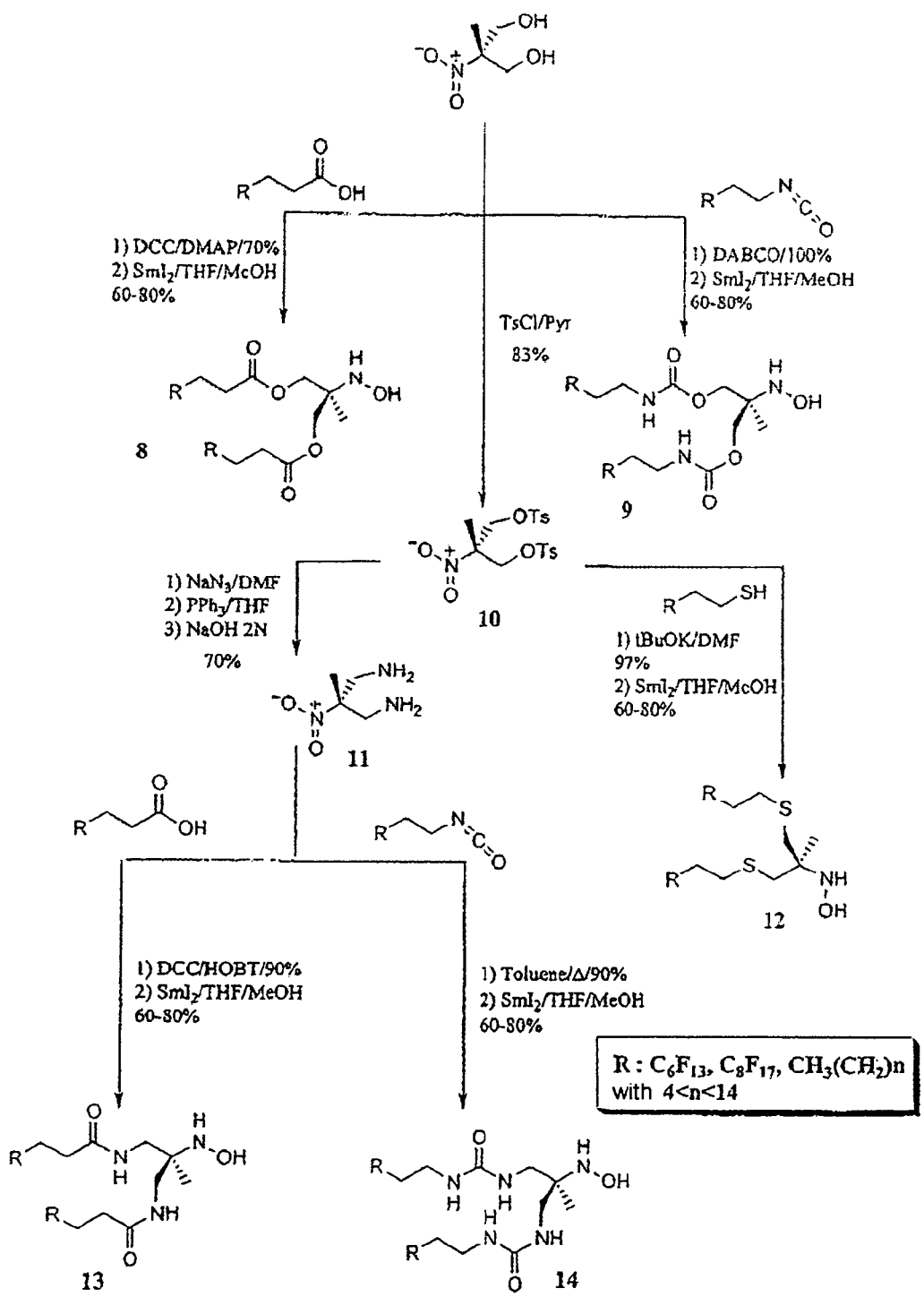
Figure 2: Synthesizing the hydrophobic bicatenary hydrocarbon and perfluorocarbon moieties

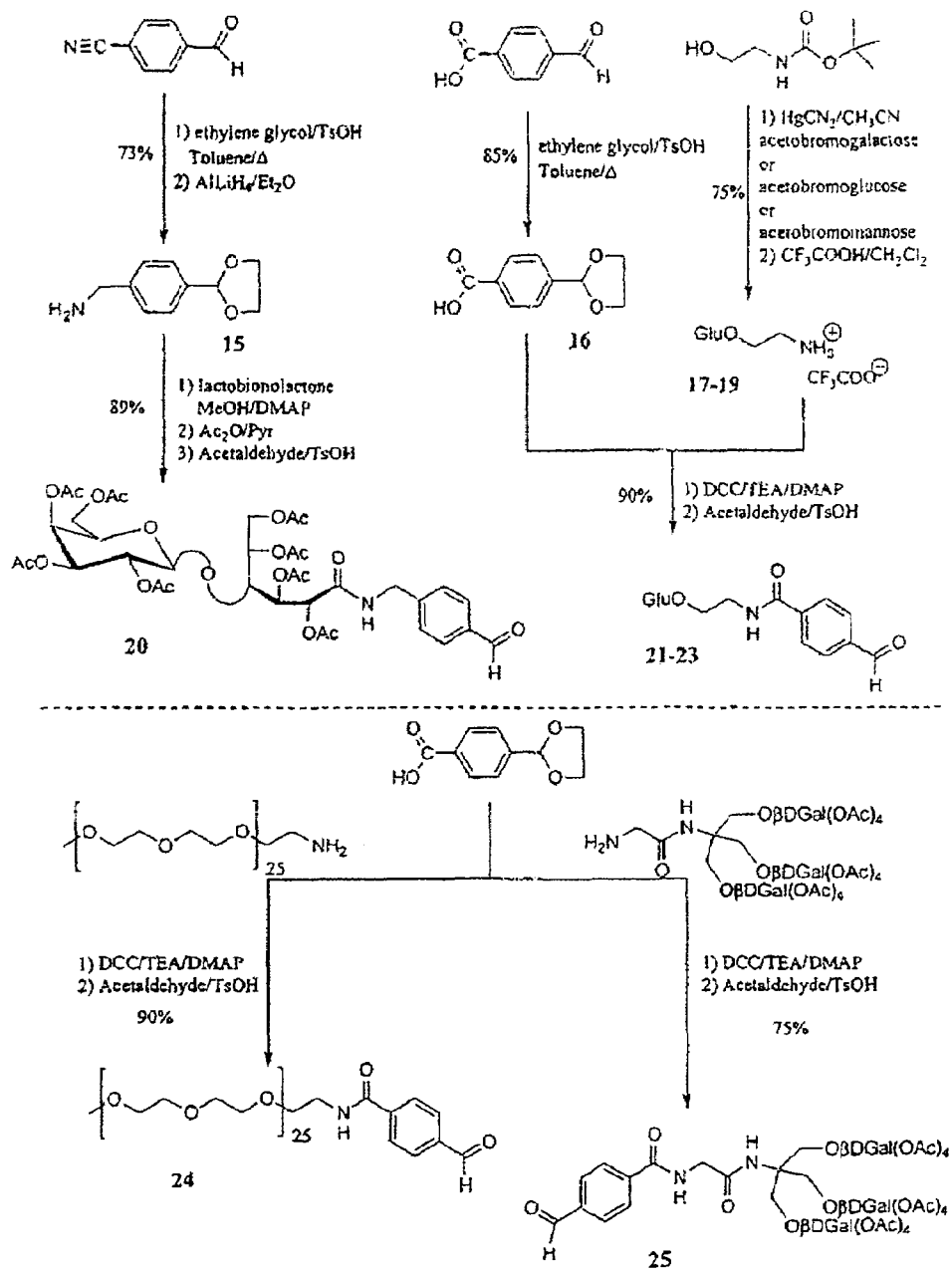
Figure 3: Synthesizing the nonionic polar heads

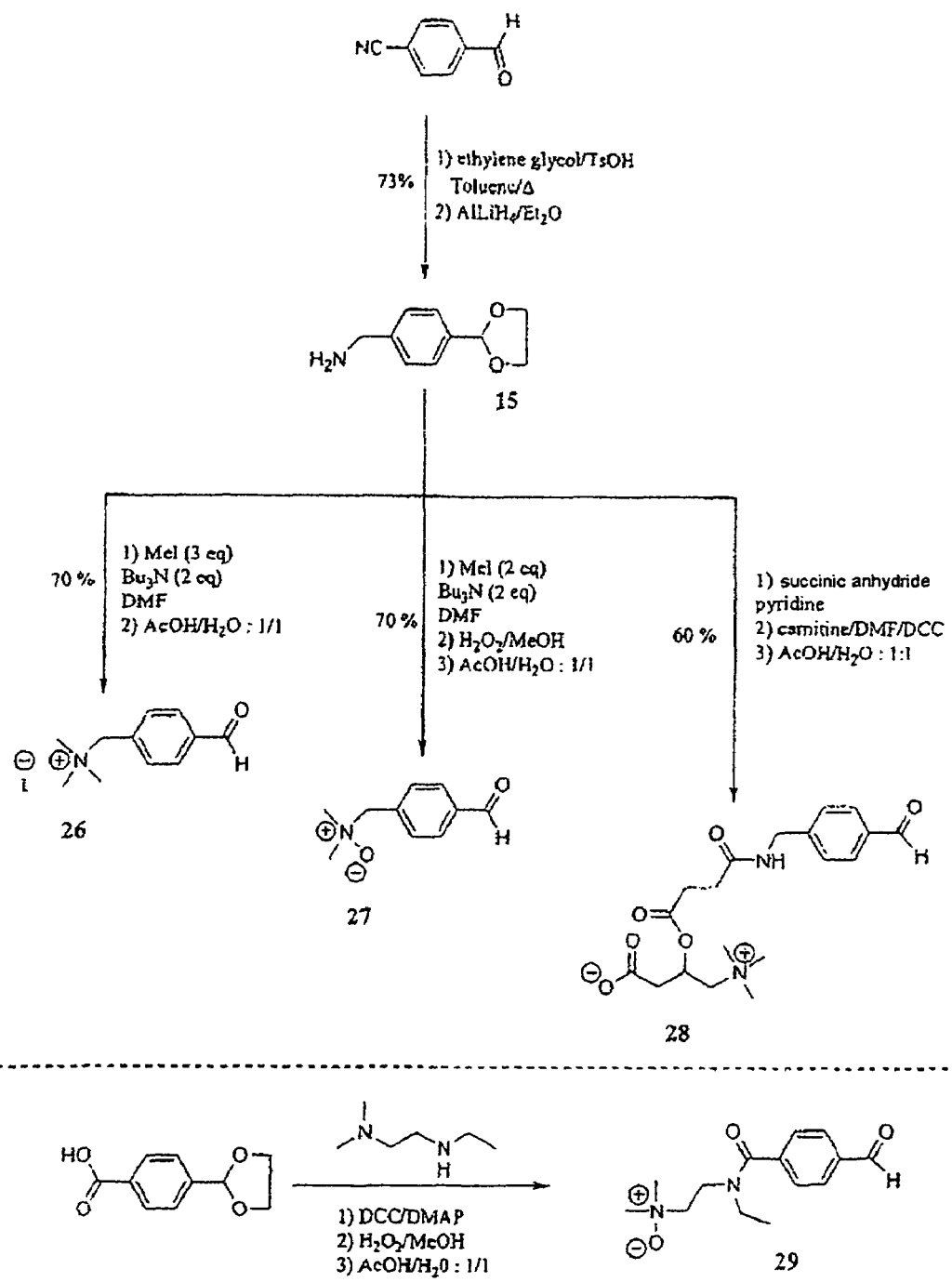
Figure 4: Synthesizing the ionic polar heads

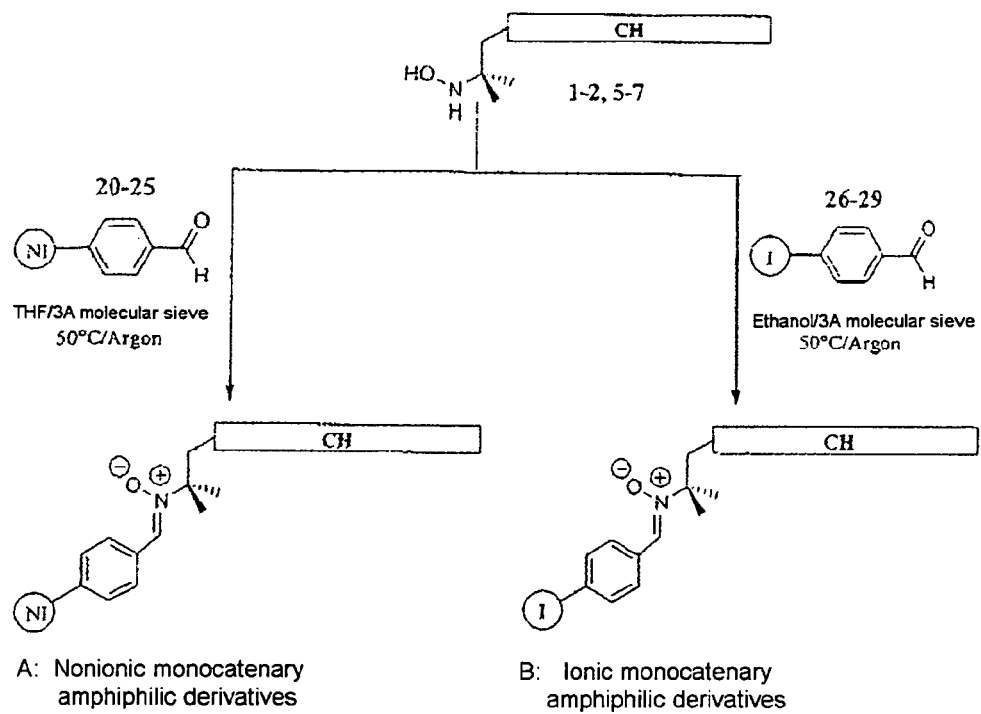
Figure 5: Synthesizing the monocatenary amphiphilic nitrones A-B

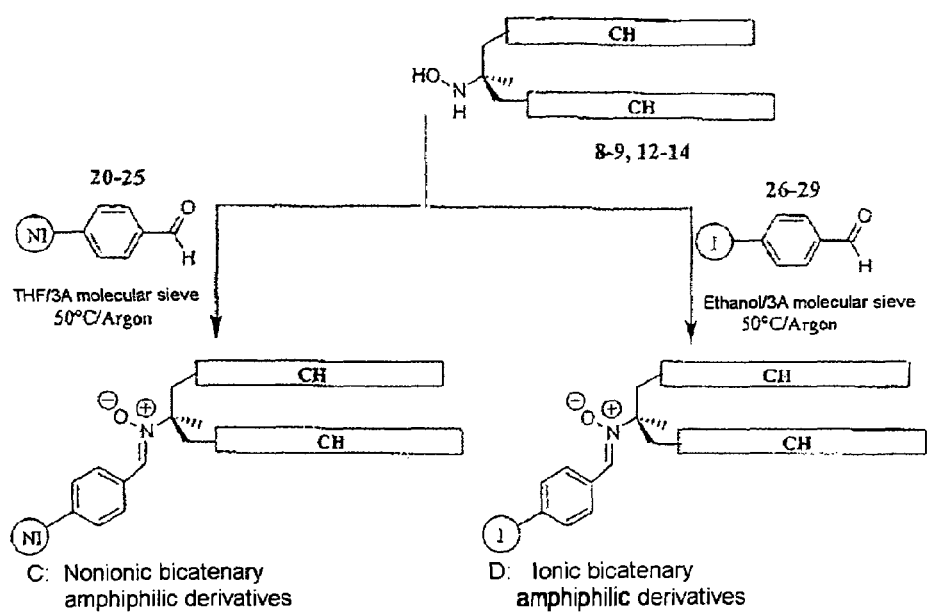
Figure 6: Synthesizing the bicatenary amphiphilic nitrones C-D

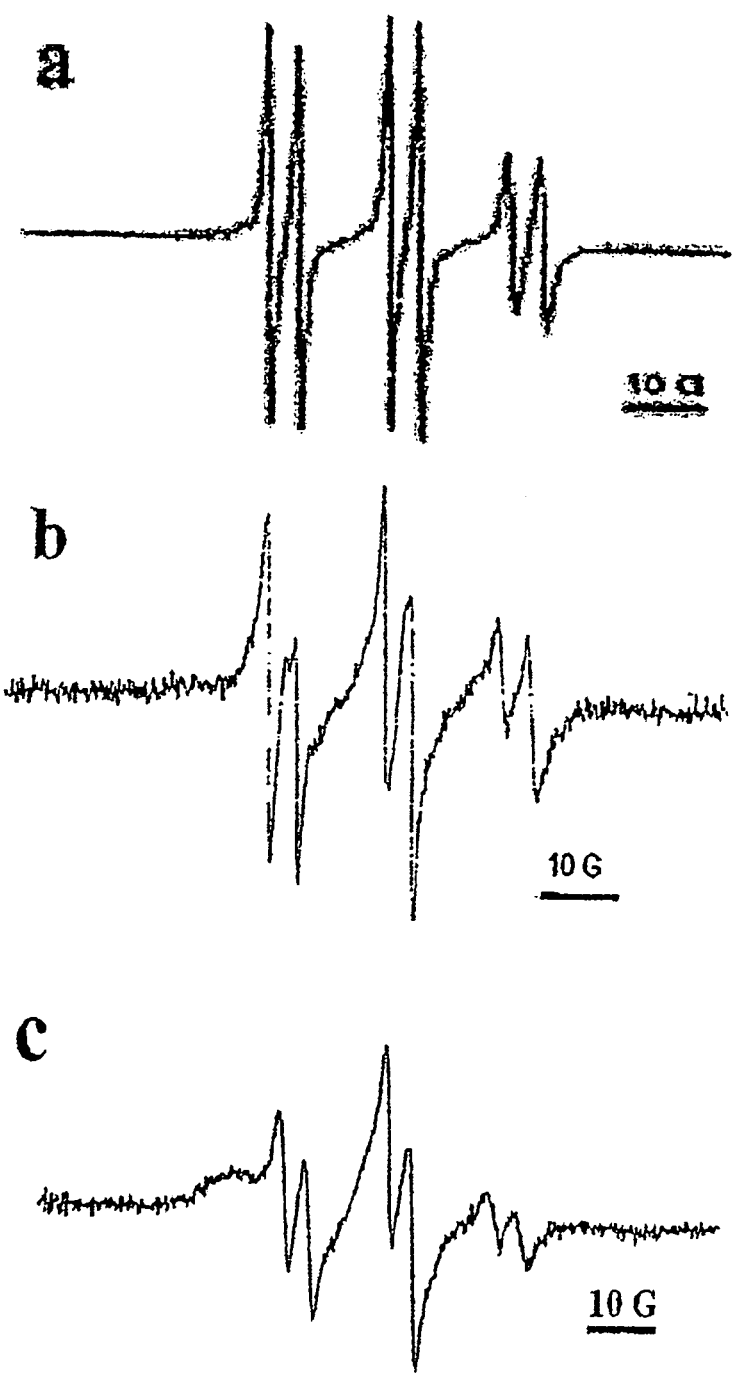
Figure 7: EPR spectra of the carboxylate (a), hydroxyl (b) and methyl (c) adducts which are respectively generated by the Fenton reaction (b) in the presence of formate (a) and of DMSO (c) and of the compound $A_1$

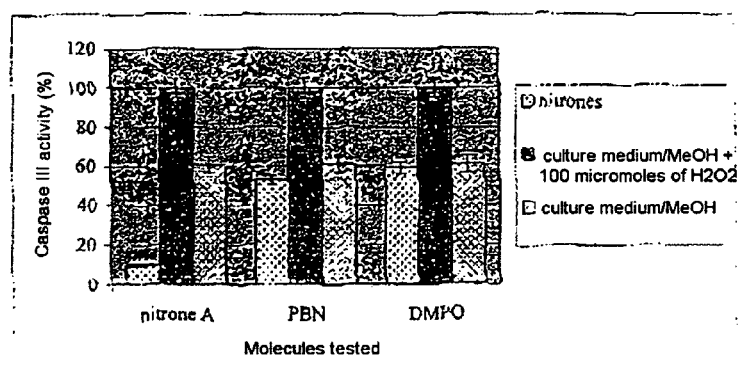
Figure 8: Caspase III activity of neuronal cells which have been poisoned with $H_2O_2$ and treated with commercial nitrones and the type A2 nitrone

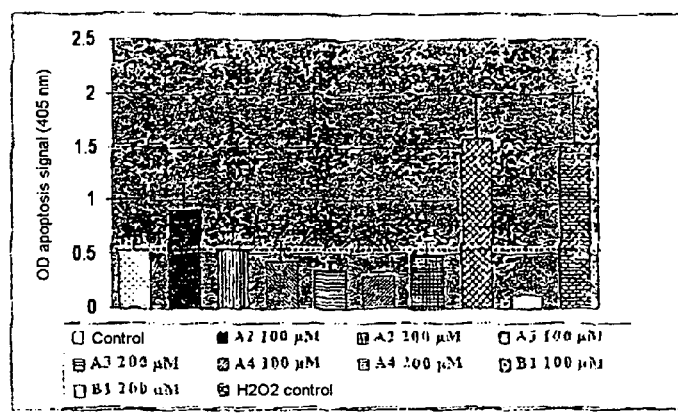
Figure 9: Measuring the state of apoptosis by means of an ELISA assay of the fragmentation of the DNA following lysis of the cells

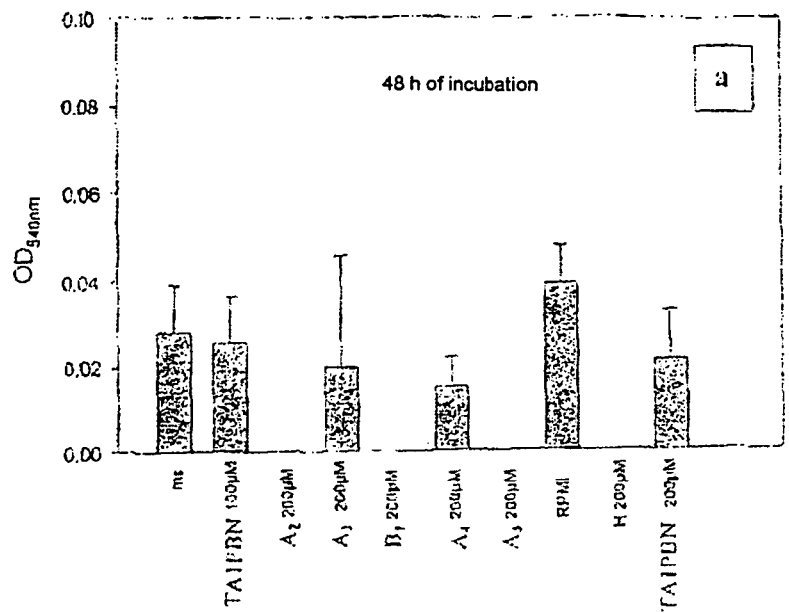
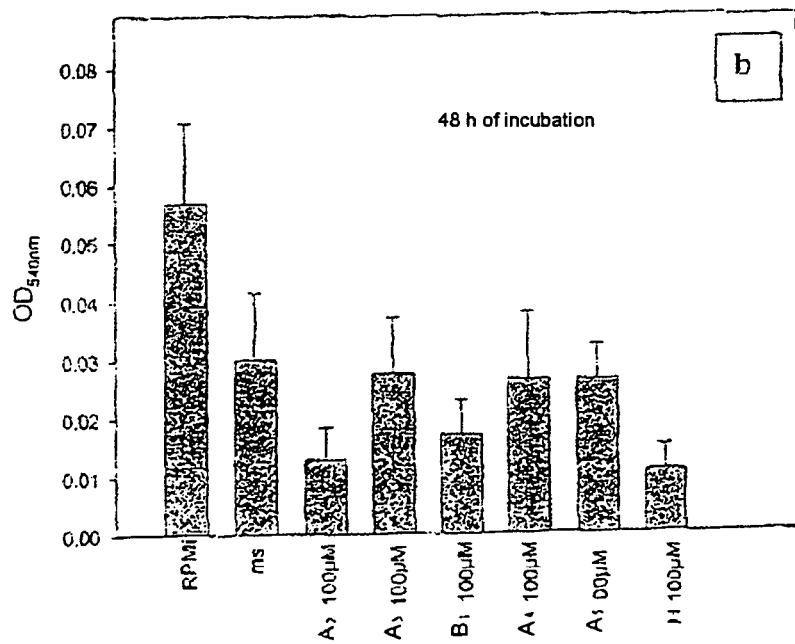
Figures 10a and 10b: Culture of NARP cells in the presence of 100 (a) and 200 μM (b) amphiphilic nitrones after 48 h of incubation

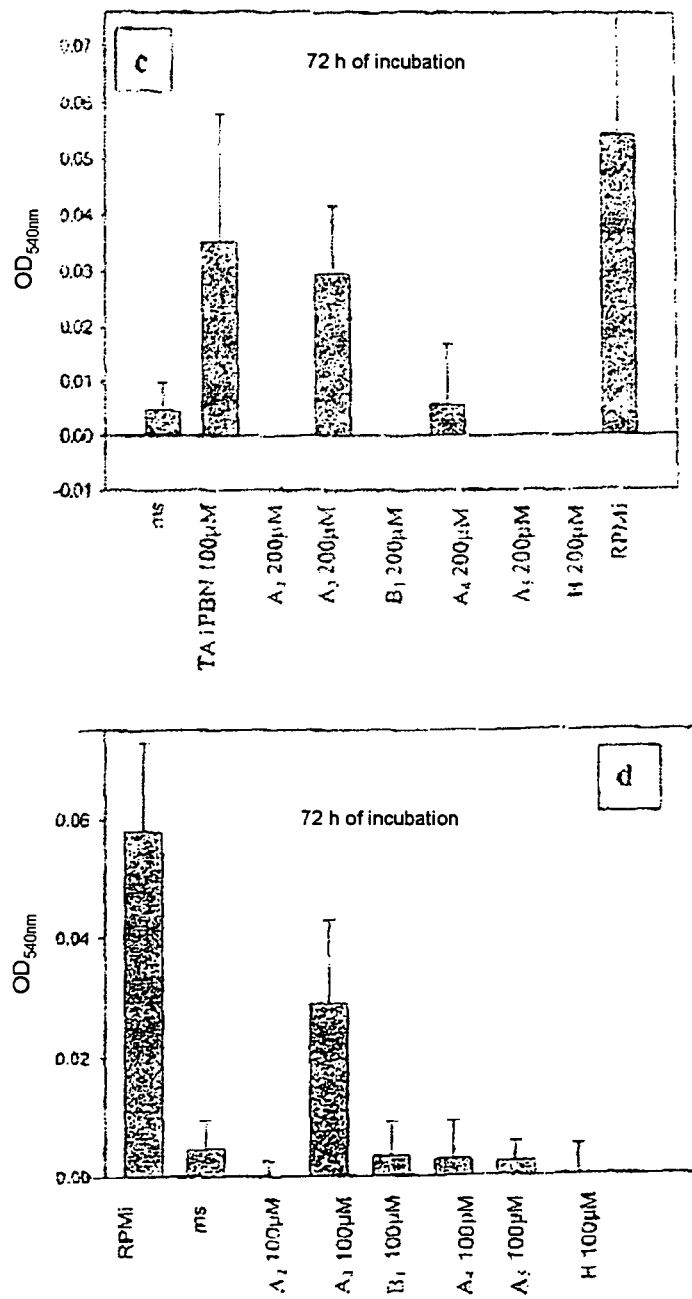
Figures 10c and 10d: Culture of NARP cells in the presence of 100 (d) and 200 µM (c) amphiphilic nitrones after 72 h of incubation

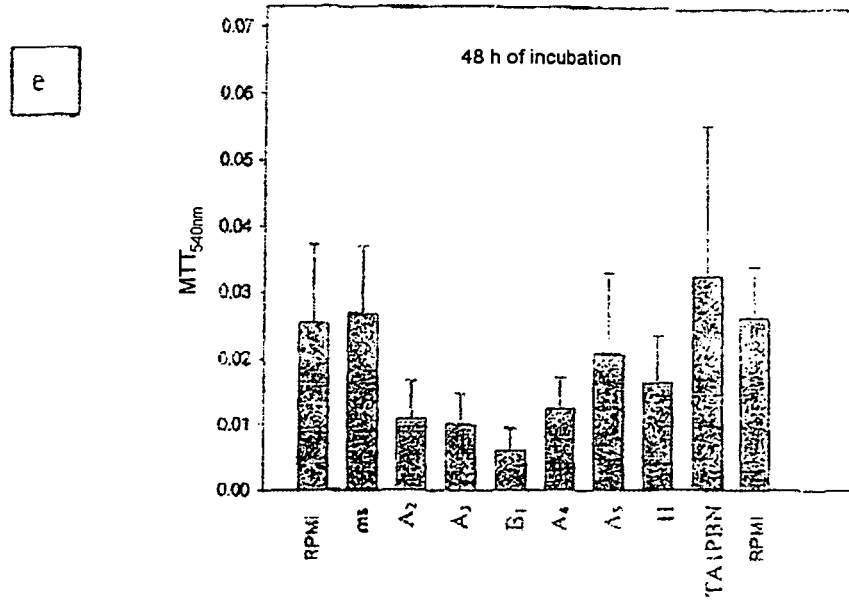
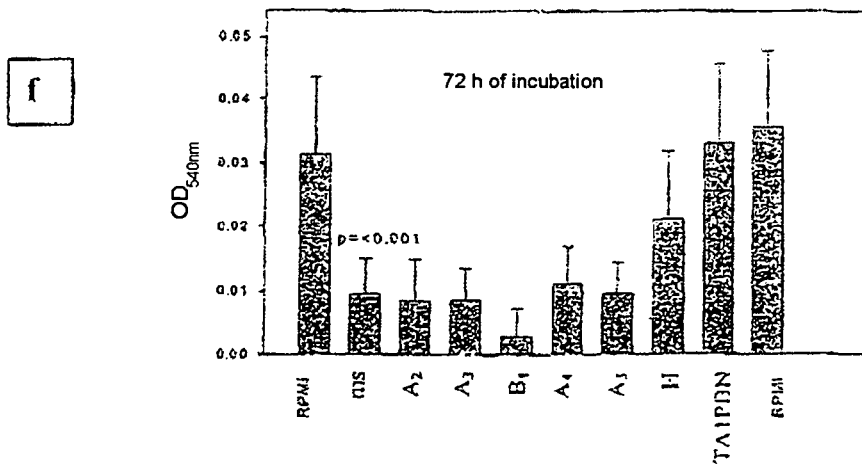
Figures 10e and 10f: Culture of NARP cells in the presence of 50 µM amphiphilic nitrones after 48 h (e) and 72 h (f) of incubation

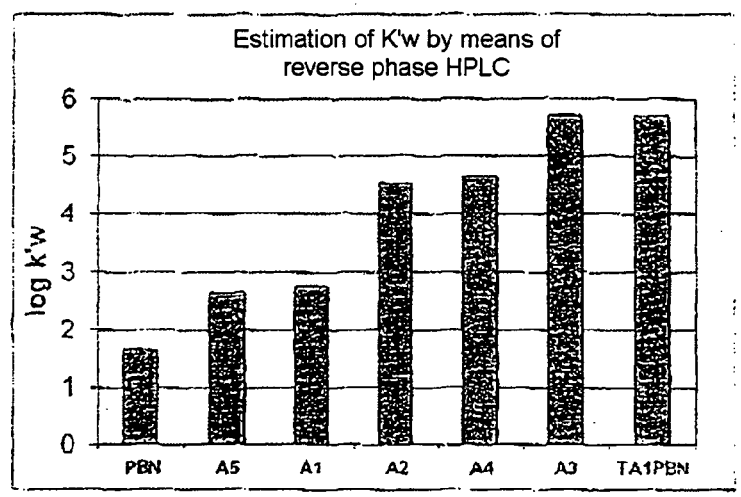
Figure 11: Variation in the hydrophobicity of the lactobionic acid-derived nitrones A1-A5.

AMPHIPHILIC DERIVATIVES OF α-C-PHENYL-N-TERT-BUTYLNITRONE

CROSS REFERENCE TO RELATED APPLICATIONS

This application is a national stage application filed under 35 U.S.C. 371 of International Application No. PCT/FR2003/003335, filed Nov. 7, 2003, which claims priority from French patent application 02 14078, filed Nov. 8, 2002.

The invention relates to novel compounds which are derived from α-C-phenyl-N-tert-butylnitrone, to a process for preparing them and to their use for preparing drugs which are intended to prevent or treat the diseases linked to oxidative stress.

The pathological conditions linked to oxidative stress and the formation of oxygen-containing free radical species have been listed by Croos C. E., *Arch, Intern. Med.* (1987) 107, 526-545 and by Anderson K. M., Ells G., Bonomi P., Harris J. E., *Medical Hypotheses* (1999) 52, 53-57.

There are a large number of them: more than 70 pathological conditions of this type are cited in this list, which includes, in particular, immune and inflammatory diseases, the ischemia-reperfusion syndrome, atherosclerosis, Alzheimer's and Parkinson's diseases, lesions due to UV and ionizing radiations, certain forms of chemical carcinogenesis and cellular aging.

The oxygen-containing and nitrogen-containing free radical species (ROS and RNS) are produced naturally in the body and they are regulated by certain specialized enzymes such as soluble superoxide dismutase (sSOD). It is vitally important that these extremely reactive free radical species be trapped since they cause irreversible damage in the cell. Whereas the normal production of these free radical species is easily regulated by the cell, overproduction of free radicals linked to an external oxidative stress (inflammatory shock, ischemia-reperfusion syndrome, etc.) or a genetic deficiency (mitochondrial anomaly, in particular) causes rapid breakdown of the cell. It then becomes impossible for the human or animal body to deal with this substantial influx of free radicals.

Several mechanisms exist for defending against oxidative stress in the cell, with these mechanisms being able to exert an effect at different levels in the oxidative cascade. This latter is generally initiated by the overproduction of superoxide free radicals linked to partial reduction of the molecular oxygen in the mitochondrion (typical syndrome of ischemia reperfusion). This superoxide free radical can dismutate into hydrogen peroxide. These two species can, by way of Fenton's reaction and in the presence of ferrous iron, give rise to hydroxyl free radicals, which have the special characteristic of reacting very rapidly and nonspecifically with any of the constituents of the cell such as lipids, DNA or proteins, causing irreversible damage among these constituents, as has been described by Stadtman H. R., Berlett B. S. *J. Biol. Chem.* (1991) 266, 17201-17211; Floyd R. A. *Carcinogenesis* (1990) 11, 1447-1450; Gille J. J., Van Berkel C. G., Joenge H. *Carcinogenesis* (1994) 15, 2695-2699; Halliwell B. *Mutat. Res.* (1999) 443, 37-52.

By activating certain suicide genes (Bel or p53 genes) by way of the NF-kB factor, these free radical species are also responsible for the phenomenon of cellular apoptosis which has been described by Siebenlist U., Franzoso G., Brown K. *Annu. Rev. Cell. Biol.* (1994) 10, 405-455.

The soluble SOD is responsible for converting the superoxide free radical into hydrogen peroxide, with this latter then being dealt with by glutathione-dependent peroxidases or catalases.

Other levels of cellular protection against oxidizing agents exist, particularly in the membrane, with these levels of protection limiting the oxidation of the unsaturated membrane phospholipids. α-Tocopherol and β-carotene are the main examples of lipid anti-oxidants.

The most promising strategy in searching for a therapy which is intended to prevent or treat the diseases linked to oxidative stress consists in intervening as far upstream as possible in this oxidative cascade in order to prevent, at a very early stage, the damage which is linked to the very powerful reactivity of the free radical species.

In order to do this, attempts have been made to trap these highly reactive free radicals by way of what are termed "spin-trap" molecules, of which the nitrones appear to be the most effective.

The therapeutic effect of nitrones in the reduction and prevention of the damage caused by free radicals in biological systems was demonstrated in 1990 by Oliver C., Starke-Read P., Stadman E., Liu G., Carncy J., Floyd R. *Proc. Natl. Acad. USA* (1990) 87, 5144-5147.

These authors demonstrated a decrease in the damage caused by cerebral ischemia in gerbils after α-C-phenyl-N-tert-butylnitrone (PBN) had been injected. Cerebral ischemias are accompanied by a large increase in the production of free radicals, which were trapped by the PBN, thereby forming spin adducts which were much more stable and therefore less reactive and toxic. PBN is the spin trap to which the largest number of biological studies have related.

Reference may be made, for example, to Hensley K., Carney J. M., Stewart C. A., Tabatabaie T., Pye Q. N., Floyd R. A. *Int. Rev. Neurobiol.* (1997) 40, 229-317.

PBN possesses a very high degree of specificity for acting in the brain, with this probably being due to its substantial hydrophobicity, which enables it to cross the blood-brain barrier, as has been demonstrated by Cheng H. Y., Liu T., Feuerstein G., Barone F. C. *Free Radic. Biol. Med.* (1993) 14, 243-250.

The most well-known and effective nitrones are α-C-phenyl-N-tert-butylnitrone (PBN), 5,5-dimethyl-pyrrolidine N-oxide (DMPO) and more recently discovered molecules: N-benzylidene-1-diethoxyphosphoryl-1-methyl-ethylamine N-oxide (PBNP) and 5-diethylphosphono-5-methylpyrroline N-oxide (DEPMPO).

A disulfonate derivative of PBN, i.e. NXY-059 (disodium 4-[(tert-butylimino)methylbenzene-1,3-di-sulfonate N-oxide), which possesses a neuroprotective activity which is greater than that of PBN, and which is in the course of pharmacological study and clinical development, may also be mentioned:

Kuroda S., Tsuchidate R., Smith M. L., Maples K. R., Siesjo B. K. *J. Cereb. Blood Flow Metab.* (1999) 19, 778-787;

Lees K. R., Sharma A. K., Barer D., Ford G. A., Kostulas V., Cheng Y. F., Odergren T. *Stroke* (2001) 32, 675-680.

However, none of the abovementioned compounds possesses a satisfactory in-vivo or ex-vivo efficacy at low dosage, even if their cytotoxic concentration is very high: Almli L. M., Hamrick S. E. G., Koshy A. A., Täuber M. G., Ferriero D. M. *Dev. Brain Res.* (2001) 132, 121-129; Nakao N., Grasbon-Frodl E. M., Widner H., Brundin P. *Neuroscience* (1996) 73, 185-200. This lack of efficacy is probably linked to poor bioavailability of the drug and to a problem of cell penetration.

There remains, therefore, the need for a spin-trap compound which is able to trap free radicals and which can also be transported by the human or animal body to its target within the cell.

In particular, there remains the need for a compound which is able to traverse the cell membrane and, what is an even more significant and difficult challenge, the mitochondrial membrane in order to enter the compartment in which the superoxide free radical is produced.

With this aim in view, Ouari O., Polidori A., Pucci B., Tordo P., Chalier F. *J. Org. Chem.* (1999) 64, 3554-3556 and Geromel V., Kadhom N., Celabos-Pico I., Ouari O., Polidori A., Munnich A., Rötig A., Rustin P. *Hum. Mol. Genet.* (2001) 10, 1221-1228 have suggested an amphiphilic perfluorocarbon derivative of PBN: TA1PBN.

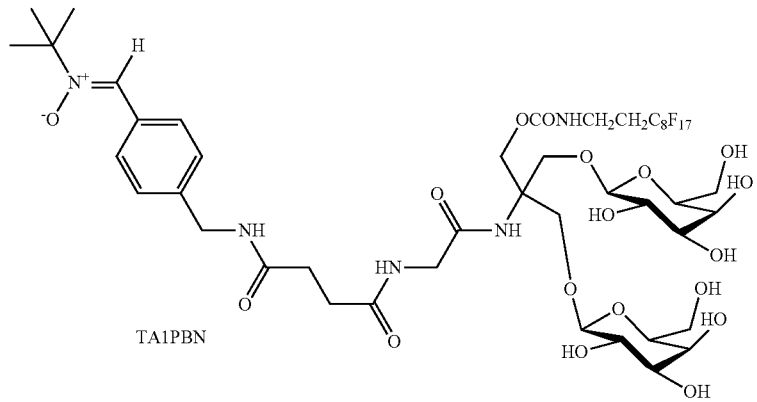

TA1PBN

This compound has been tested on fibroblast cell lines suffering from a severe deficiency in the activity of the V complex of the respiratory chain (ATPase) and it has given encouraging results.

However, the synthesis of TA1PBN presents difficulties which make it difficult to envisage producing it on an industrial scale.

Consequently, the applicant set itself the objective of conceiving and making novel compounds which possess spin-trap activity, which exhibit a bioavailability which is increased as compared with that of the molecules of the prior art and whose preparation is simple, thereby making it possible to envisage production on an industrial scale.

The invention relates to novel compounds which are characterized in that they correspond to the following formula (I):

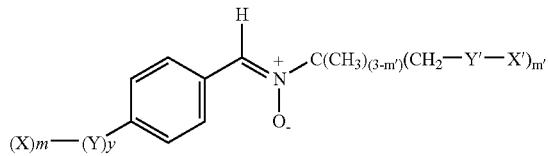

(I)

in which:

X represents a hydrophilic group which is selected from a monosaccharide or a polysaccharide as well as amino derivatives of monosaccharides and polysaccharides, a poly(etylene oxide) chain, a peptide chain, a polar ionic group selected from a quaternary ammonium, an amine oxide, or a carnitine group;

m represents an integer equal to 1, 2 or 3;

Y represents a spacer arm which is intended to link the aromatic nucleus to the hydrophilic X substituents;

Y is selected from ester, amide, urea, urethane, ether, thioether and amine functions, and $C_1$-$C_6$ hydrocarbon chains which are optionally interrupted by one or more ester, amide, urea or urethane functions and by one or more ether, amine or thioether bridges;

y represents an integer equal to 0 or to 1;

Y' represents a group selected from a

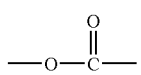

ester function, a

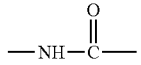

amide function, a

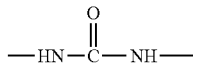

urea function, a

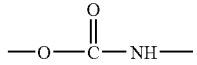

urethane function, an —O— ether bridge or an —S— thioether bridge;

m' is an integer selected from 1 and 2;

X' represents a hydrogen atom or a $C_4$-$C_{14}$ alkyl chain which is optionally substituted by one or more fluorine atoms.

Of the monosaccharides which can be used in the present invention, mention may be made of glucose, lactose, fructose, mannose, galactose, ribose and maltose. Of the amino derivatives of sugars, mention may be made, in particular, of glucosamine. Of the polysaccharides which can be used in the present invention, mention may be made of the chains consisting of several monosaccharide units, such as: sucrose and lactobionamide.

When the hydrophilic part X of the molecule of the formula (I) is a poly(etylene oxide) chain, this latter advantageously comprises from 30 to 100 ethylene oxide units, preferably from 50 to 60 units.

The peptide chain preferably consists of natural amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

Hydrophilic ionic and nonionic groups which can be used in the present invention are illustrated in scheme 1 below.

Scheme 1:
General structures of the polar heads

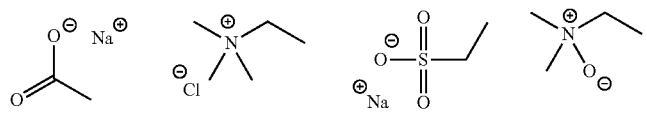

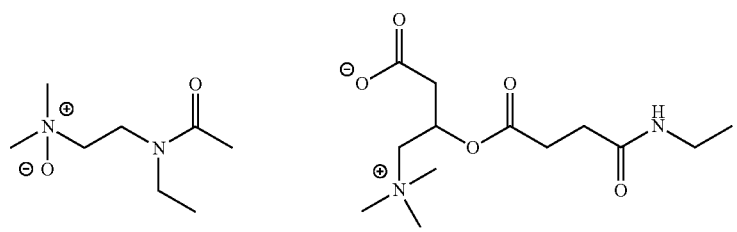

Ionic polar heads

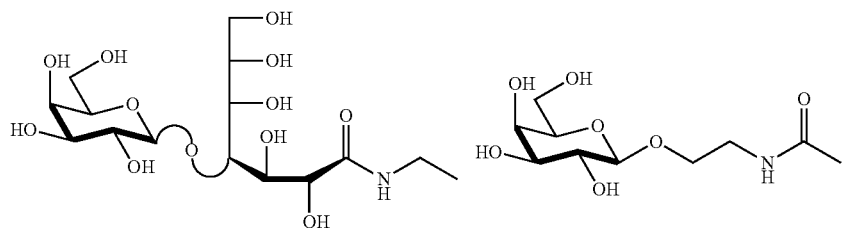

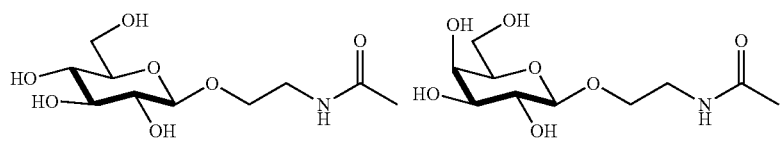

-continued

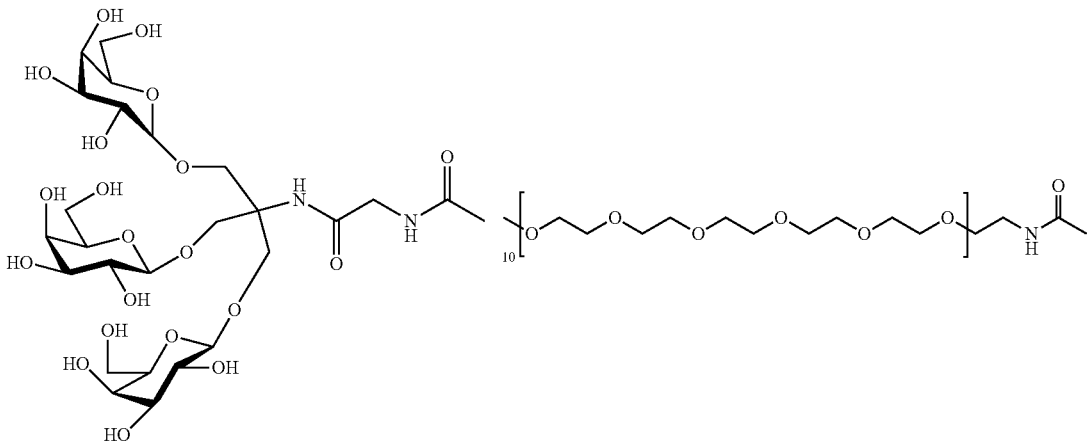

Nonionic polar heads

The spacer arm Y is substituted once or twice by the group X depending on whether the spacer arm is monofunctional or multifunctional.

The group X' can be selected, for example, from the following radicals:

hydrocarbon radicals: n-butyl, tert-butyl, isobutyl, n-pentyl, isopentyl, n-hexyl, n-heptyl, n-octyl, n-nonyl, n-decyl, n-undecyl, n-dodecyl, n-tri-decyl, n-tetradecyl, etc., fluorinated hydrocarbon radicals: those which may be mentioned correspond to the formula $-(CH_2)_t-(CF_2)_rF$, in which r and t represent two integers where: $14 \geq r+t \geq 4$, such as, for example:

$(CF_2)_4F$; $-(CF_2)_5F$; $-(CF_2)_6F$; $-(CF_2)_7F$; $-(CF_2)_8F$; $-(CF_2)_9F$; $-(CF_2)_{10}F$; $-(CF_2)_{11}F$; $-(CF_2)_{12}F$; $-(CF_2)_{13}F$; $-(CF_2)_{14}F$; $-CH_2-(CF_2)_3F$; $-CH_2-(CF_2)_4F$; $-CH_2-(CF_2)_5F$; $-CH_2-(CF_2)_6F$; $-CH_2-(CF_2)_7F$; $-CH_2-(CF_2)_8F$; $-CH_2-(CF_2)_9F$; $-CH_2-(CF_2)_{10}F$; $-CH_2-(CF_2)_{11}F$; $-CH_2(CF_2)_{12}F$; $-(CH_2)-(CF_2)_{13}F$; $-(CH_2)_2-(CF_2)_2F$; $-(CH_2)_2-(CF_2)_3F$; $-(CH_2)_2-(CF_2)_4F$; $-(CH_2)_2-(CF_2)_5F$; $-(CH_2)_2-(CF_2)_6F$; $-(CH_2)_2-(CF_2)_7F$; $-(CH_2)_2-(CF_2)_8F$; $-(CH_2)_2(CF_2)_9F$; $-(CH_2)_2-(CF_2)_{10}F$; $-(CH_2)_2-(CF_2)_{11}F$; $-(CH_2)_2-(CF_2)_{12}F$; $-(CH_2)_3(CF_2)_1F$; etc., $-(CH_2)_{13}-(CF_2)F$.

At least one of the following conditions is preferably satisfied:

X represents a lactobionamide group, carnitine or a polyoxyethylene chain;

m represents 1;

m' represents 1 or 2;

X' is selected from octyl, decyl, dodecyl or $CF_3(CF_2)_rCH_2CH_2-$, where $8 \geq r \geq 6$.

The compounds of the invention exhibit the advantage, as compared with the compounds of the prior art, of being endowed with a superior bioavailability. This superior bioavailability is at least in part attributable to the amphiphilic nature of the molecules of the invention.

The invention also relates to a process for preparing the compounds corresponding to the formula (I), with this process being characterized in that an aldehyde corresponding to the formula (II) is reacted with a hydroxylamine corresponding to the formula (III) in accordance with scheme 2 below:

Scheme 2

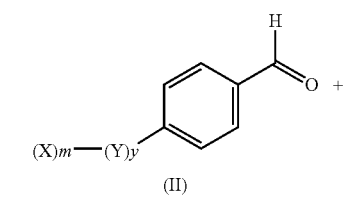

(II)

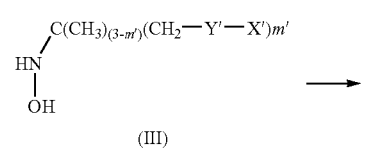

(III)

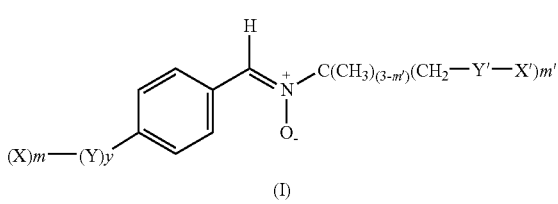

(I)

in which X, y, Y, m, X', m' and Y' have the same definition as above.

The compounds of the formula (III) are prepared in accordance with a process which is described in scheme 3 below:

Scheme 3

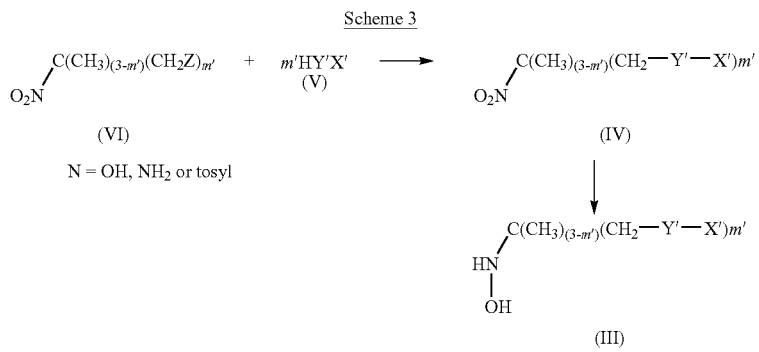

N = OH, NH₂ or tosyl

Scheme 3 is implemented under conditions which will be explained below, with these conditions depending on the nature of the lipophilic group.

BRIEF DESCRIPTION OF THE DRAWINGS

FIG. 1 illustrates an alternative embodiment of the preparation of compounds of the formula (III);

FIG. 2 illustrates an alternative embodiment of the preparation of compounds of the formula (III);

FIG. 3 illustrates the preparation of compounds of formula (II) in accordance with an embodiment of the present invention;

FIG. 4 illustrates the preparation of the compounds of formula (II) in accordance with an embodiment of the present invention;

FIG. 5 illustrates the synthesizing of the monocatenary amphiphilic nitrones A-B;

FIG. 6 illustrates the synthesizing of the bicatenary amphiphilic nitrones C-D;

FIG. 7 illustrates the EPR spectra of the carboxylate (a), hydroxyl (b) methyl (c) adducts which are respectively generated by the Fenton reaction (b) in the presence of formate (a) and of DMSO (c) and of the compound $A_1$;

FIG. 8 is a bar graph illustrating caspase III activity of neuronal cells which have been poisoned with $H_2O_2$ and treated with commercial nitrones and the type $A_2$ nitrone;

FIG. 9 is a bar graph depicting the measured state of apoptosis by means of an ELISA assay of the fragmentation of the DNA following lysis of the cells;

FIGS. 10a and 10b are bar graphs depicting the culture of NARP cells in the presence of 100(a) and 200 µM (b) amphiphilic nitrones after 48 hours of incubation;

FIGS. 10c and 10d are bar graphs depicting the culture of NARP cells in the presence of 100(d) and 200 µM (c) amphiphilic nitrones after 72 hours of incubation; and FIGS. 10e and 10f are bar graphs depicting the culture of NARP cells in the presence of 50 µM amphiphilic nitrones after 48 hours of incubation (e) and 72 hours (f) of incubation.

FIG. 11 is a bar graph depicting variation in the hydrophobicity of the lactobionic acid-derived nitrones A1-A5.

a—HYDROPHOBIC MONOCATENARY HYDROCARBON OR PERFLUOROCARBON MOIETY (FIG. 1):

FIG. 1 illustrates the preparation of the compounds of the formula (III) where:

m'=1;
X'=(CH₂)₂—R where R=$C_6F_{13}$, $C_8F_{17}$ or $CH_3(CH_2)_n$, where 4<n<14.

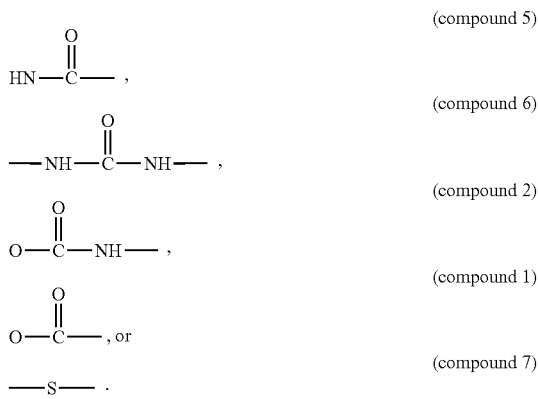

The hydrophobic monocatenary moiety is synthesized from 2-methyl-2-nitropropanol. The alcohol function of this synthon makes it possible to attach the hydrocarbon and perfluorocarbon chains directly by way of ester bonds, by reacting the alcohol and the acid in the presence of a coupling agent, dicyclohexyl-carbodiimide and dimethylaminopyridine (1).

The alcohol can also react with an alkyl isocyanate in order to give bonds of the urethane type (2).

The alcohol function can be converted into an amine by tosylation followed by replacement with sodium azide. By means of a Staudinger reaction, the alkyl azide is transformed into an amine in the presence of triphenylphosphine and sodium hydroxide.

This amine can react with a fatty acid in order to give a bond of the amide type (5), or with an alkyl isocyanate in order to form a urea (6).

Finally, the tosylate can be replaced, in basic medium, with a thiol in order to form a thioether bond (7).

The nitro function of the different hydrophobic synthons (1-7) is then reduced to hydroxyl-amine using 4 equivalents of the Kagan reagent (SmI2) in a THF/MeOH mixture or in acetic acid.

This reaction has been described by Girard P., Namy J. L., Kagan H. B. *J. Am. Chem. Soc.* (1980) 102, 2693-2698 and Namy J. L., Girard P., Kagan H. B. *Nouv. J. Chem.* (1977) 1, 5.

The very rapid reaction (3 min) takes place with a yield varying between 50 and 100% depending on the nature of the nitroalkyl to be reduced.

b—HYDROPHOBIC BICATENARY HYDROCARBON OR PERFLUOROCARBON MOIETY (FIG. 2)

FIG. 2 illustrates the preparation of the compounds of the formula (III) where:

m'=2;
X'=$(CH_2)_2$—R where R=$C_6F_{13}$, $C_8F_{17}$ or $CH_3(CH_2)_n$, where 4<n<14;
Y'=

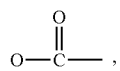 (compound 8)

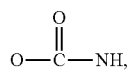 (compound 9)

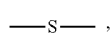 (compound 12)

(compound 14)

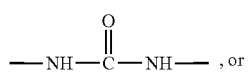 , or (compound 13)

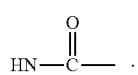 .

The hydrophobic bicatenary moieties are synthesized from 2-nitro-2-methyl-1,3-propanediol. The fatty chains are attached to the alcohol functions by means of urethane (9) or ester (8) bonds. The alcohol functions are converted into tosylate by reaction with tosyl chloride. The ditosylate can be replaced with an alkyl mercaptan in order to give a thioether (12). This ditosylate can be converted into a diamine by replacement of the tosylate with sodium azide and reaction with triphenylphosphine and alkaline hydrolysis. This diamine can react with an isocyanate in order to give a urea bond (14) or with an acid in order to form an amide bond (13).

The nitro function of the biantennary synthons is then reduced with Kagan's reagent, giving a yield which can vary from 60 to 80% depending on the molecule concerned.

c—NONIONIC HYDROPHILIC MOIETY (FIG. 3)

FIG. 3 illustrates the preparation of the compounds of the formula (II) in which:

X represents a nonionic polar group;
Y represents —NH—$CH_2$— (compound 20), (compounds 21, 22, and 23)

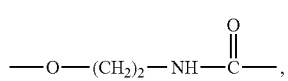 , compound 24)

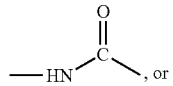 , or

-continued

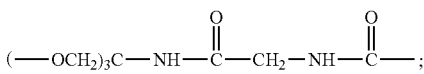 (compound 25)

y=1;
m=1 (compounds 20 to 24);
m=3 (compound 25).

The nonionic hydrophilic heads consist of sugars (lactobionamide, galactose, glucose, mannose, etc.), of polyols which are or are not glycosylated (such as Tris for example) or of polyethylene glycol. The derivatives of the lactobionamide 20 are synthesized from 4-cyanobenzaldehyde and lactobionolactone. After protecting the aldehyde function by means of acetalization (15), and then reducing the nitro group, the resulting amine is condensed on the lactobionolactone. Acetylating the alcohol functions and deprotecting the aldehyde function with an excess of acetaldehyde in acid medium gives the polar synthon 20.

The other polar heads are synthesized from 4-carboxybenzaldehyde. The glucosylated (21), mannosylated (22) and galactosylated (23) derivatives are obtained by condensing Boc-aminoethanol on the corresponding acetobromoglycosides (17, 18 and 19) under the conditions of the Helferich reaction. After deprotecting the amine function and condensing on the acid function in the presence of a peptide coupling agent, the 3 glycosylated polar heads 21-23 are obtained.

The pegylated derivative 24 is derived by condensing an amine-functionalized polyethylene glycol on the acid function of 4-carboxybenzaldehyde which is protected by an acetal. Deprotecting the acetal results in this derivative being obtained. Finally, it is possible to obtain a trigalactosylated derivative 25 by condensing an amine which has already been described in the literature by Polidori A., Pucci B., Zarif L., Lacombe J-M., Riess J-G., Pavia A. A., *Chem. Phys. Lipids* (1995) 77, 225-251 on the acid function of the 4-carboxybenzaldehyde.

d—IONIC HYDROPHILIC MOIETY (FIG. 4)

FIG. 4 illustrates the preparation of the compounds of formula (II) in which:

X represents an ionic polar group;
Y represents —$CH_2$— (compounds 26 and 27),

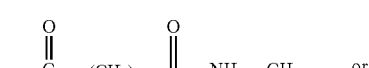 , or (compound 28)

 ; (compound 29)

y=1;
m=1.

The ionic polar heads consist of quaternary ammonium, amine oxide or carnitine groups. The ammonium group is synthesized from the nitrile after reduction with $AlLiH_4$ and prior protection of the aldehyde function with ethylene glycol. The resulting amine is permethylated with methyl iodide in the presence of tributylamine in DMF in accordance with the method described by Sommer H. Z., Lipp H. I., Jackson L. L. *J. Org. Chem.* (1971) 36, 824-828.

The crystallized product is hydrolyzed in aqueous acetic acid so as to recover the derivative 26.

The amine oxide 27 is obtained from the same amine after forming the tertiary amine in the presence of 2 equivalents of methyl iodide. The nitrogen is oxidized with 10 volumes of hydrogen peroxide in methanol. The compound 27 is obtained after deprotecting the acetal.

The amine oxide 29 is synthesized by the method of McQuade et al. from 4-carboxybenzaldehyde whose aldehyde function is protected by an acetal group and N-ethyl-N', N'-dimethylethylenediamine. This method has been described by McQuade D. T., Quinn M. A., YU S. M., Polans A. S., Krebs M. P., Gellman S. H. *Angew. Chem. Int. Ed.* (2000) 39, 758-761.

The coupling is effected in the presence of a peptide coupling agent DCC. After oxidizing the amine function with 10 volumes of hydrogen peroxide and deprotecting the acetal, compound 29 is recovered.

Finally, the carnitine derivative 28 is obtained by condensing the amine 15 on succinic anhydride and then coupling the acid function to the alcohol function of the carnitine in DMF in the presence of DCC. The product 28 is obtained after deprotecting the ketal function.

e—OBTAINING MONOCATENARY (FIG. 5) AND BICATENARY (FIG. 6) AMPHIPHILIC NITRONES

The different amphiphilic nitrones are obtained by coupling the aldehyde function of the different polar synthons to the hydroxylamine group of the hydrophobic moieties. A protic (ethanol) or aprotic (THF) polar solvent will be used depending on the more or less polar nature of the ionic hydrophilic heads (very polar), which are marked I, or nonionic glycosylated hydrophilic heads (apolar because acetylated), which are marked NI. However, the reaction is more rapid in protic polar solvents (2 days instead of 10 in THF).

In these figures, the rectangle labeled HC represents the optionally fluorinated hydrocarbon chain X'.

THF is used with glycosylated polar heads because it is a solvent which does not give rise to a reaction in which the alcohol functions are deacetylated. All the glycosylated amphiphilic nitrones were purified by reverse phase HPLC (C18 column/methanol-water eluent). The ionic compounds were isolated by crystallization. The pegylated amphiphilic nitrones are purified by exclusion chromatography (sephadex LH20).

The invention additionally relates to the use of the compounds corresponding to the formula (I) as defined above as anti-free radical agents.

Thus, it has been demonstrated that the compounds according to the present invention are endowed with an ability to trap free radicals which is equivalent to that of the compounds of the prior art.

This property makes it possible to envisage using the molecules of the invention in a variety of fields:

in the therapeutic field, the products of the invention can be used for preventing and/or treating pathological conditions linked to oxidative stress and the formation of oxygen-containing free radical species.

The invention consequently relates to pharmaceutical compositions which comprise a compound according to the invention in a pharmaceutically acceptable excipient. It relates to the use of a compound according to the invention for preparing a drug which is intended to prevent and/or treat the effects of free radicals.

The invention also relates to the use of a compound of the invention for preparing a pharmaceutical composition which is intended to prevent and/or treat pathological conditions linked to oxidative stress and to the formation of oxygen-containing free radical species, in particular immune and inflammatory diseases, the ischemia-reperfusion syndrome, atherosclerosis, Alzheimer's disease, Parkinson's disease, Huntington's disease, lesions due to UV and ionizing radiations, cancers and cellular aging.

The products of the invention can be administered by any route known to the skilled person, in particular by means of intravenous or intramuscular injection, or by means of oral or cutaneous administration. They can be used on their own or in combination with other active compounds. Their dosage, and the quantity administered daily, are adjusted in dependence on the activity which is measured in the case of the compound concerned and in dependence on the weight of the patient.

in the cosmetic field, the compounds of the invention can be used for preventing and/or treating the effects of aging as well as the effects of solar radiation.

The invention therefore also relates to a cosmetic composition which comprises a compound of the invention in a cosmetically acceptable excipient.

Said composition can be intended for application to the skin or to the epidermal appendages (nails and hair).

The composition can be present in the form of an aqueous or oily solution, of a water-in-oil or oil-in-water emulsion, of a triple emulsion or of an ointment.

The compounds of the invention can be introduced into any cosmetic composition for which anti-free radical activity is sought; a skincare cream, a sunscreen product, a makeup remover, a pack for the skin or the hair, a shampoo, a makeup product such as a lipstick, a paint, a foundation, a nail varnish, etc.

in the field of organic synthesis, the compounds of the invention can be used as free radical capturing agents in free radical reactions.

Due to their solubility in a variety of media, the compounds of the invention are easy to use and can be employed under a great variety of conditions.

EXPERIMENTAL SECTION

I—Biological Evaluation

The compound $A_1$ was used for carrying out free radical trapping experiments. Several compounds according to the invention were tested in vitro for their ability to act as biological antioxidants and anti-free radical agents.

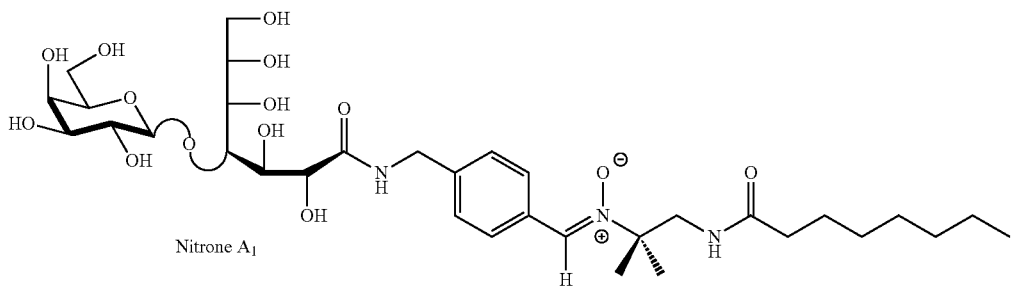

Nitrone A₁

1—Measuring the Ability to Trap Free Radical Species

The free radical trapping experiments, which were centered on carbon ($CH_3$ and $CO_2$ radicals) and oxygen (OH radical) and were carried out on compound $A_1$, demonstrated that the functionalization of the PBN did not affect the ability of these compounds to trap the free radical species. It was possible to observe EPR signals which were characteristic of the free radical species centered on carbon, as illustrated by FIG. 7.

On the other hand, when hydroxyl free radicals are generated in the system, EPR signals characteristic of the trapping of free radicals centered on carbon are detected. This is due to the trapping, by the nitrone, of carbon-containing free radicals produced on the polar heads by reaction of the OH radicals with the hydrogens of the sugars.

2—Measuring the Biological Antioxidant and Anti-Free Radical Ability In Vitro a—Evaluating the Antiapoptotic Ability on Rat Cortical Neurons by Assaying the Enzymic Activity of Caspase III These preliminary tests were carried out on a glycosylated hydrocarbon amphiphilic nitrone derivative: nitrone $A_2$. Its antiapoptotic activity was compared with that of two commercial nitrones, i.e. PBN and DMPO.

Raju S. M., Smulson M. E., Yannin T., Yu V. I., Miller D. K. *Nature* (1995) 376, 37-43).

The different compounds to be tested were incubated for 20 hours at various nontoxic concentrations (10, 100 and 200 μM) before the poisoning with hydrogen peroxide. After having been rinsed and dried in an incubator, the cells are lyzed prior to the calorimetric assay. The amphiphilic nitrone $A_2$ possesses significant cytotoxicity above 400 μM.

The results obtained (illustrated by FIG. 8) clearly show a very marked decrease in caspase III activity after poisoning with 100 μM hydrogen peroxide when the amphiphilic nitrone $A_2$ is present. This activity proves to be much lower than the normal activity of caspase III in neuronal cells which are not poisoned. The results clearly indicate a level of protection which is superior to that which is measured in the case of the commercial nitrones PBN and DMPO.

b—Assessing the Neuroprotective Efficacy on Nerve-Muscle Cocultures

The protective effect of these amphiphilic nitrones was assessed on nerve-muscle cocultures following poisoning with hydrogen peroxide for 30 min.

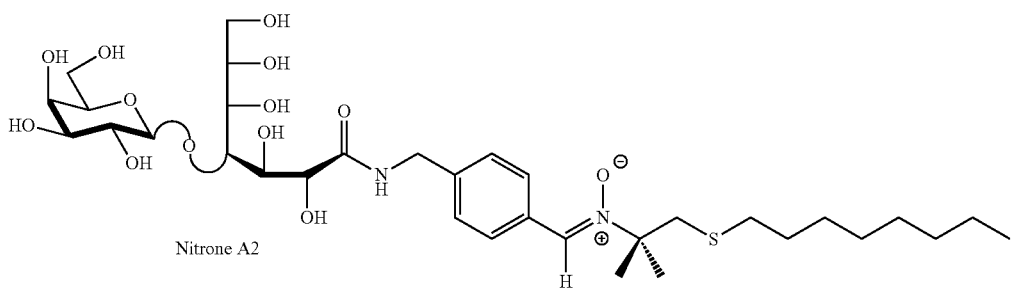

Nitrone A2

The rat neuronal cells were poisoned for 20 min with 100 μM hydrogen peroxide on the 8th day of culture. This addition of hydrogen peroxide creates a phenomenon of apoptosis as has been described by Whittemore E. R., Loo D. T., Cotman C. W. *Neuroreport* (1994) 5, 1485-1488 (verified by means of a positive control for apoptosis produced by adding staurosporin), with the apoptosis being assessed by the calorimetric assay, at 405 nm, of an enzyme which is specific for this metabolism, i.e. caspase III, in comparison to a maximum poisoning control (previously described by Nicholson D. W., Ali A., Thornbury N. A., Vaillancourt J. P., Ding C. H., Gallant M., Griffin P. R., Labelle M., Lazebnik Y. A., Munday N. A., The human muscle cells, derived from samples of healthy striated muscles, are isolated by migration of satellite cells into an appropriate culture medium. These cells fuse to form noncontractile muscle fibers in the culture medium. Explants of rat embryo spinal cord are deposited on the muscle cells.

After three weeks, all the muscle fibers in the vicinity of the explants contract and possess mature neuromuscular junctions. Following maturation, these cells are selected and filmed with a video camera coupled to a microscope. The compounds of the A ($A_1$, $A_2$, $A_3$ and $A_4$) and B ($B_1$) type are incubated for 20 h at concentrations of 100 and 200 μM. The cells are then poisoned for 30 min with 800 mM $H_2O_2$, after which they are rinsed. At 24 h and 48 h after this oxidative stress has been generated, the cells are observed and filmed.

After 20 h of incubation, it can be seen that the ionic compound $B_1$, which is of the carboxylate type, is cytotoxic and causes rapid breakdown of the muscle cells. While the other compounds are not toxic, they give rise to a cessation, or a deceleration, of the muscle contractions, whatever the contraction employed (100 and 200 μM). On the other hand, total or partial recovery of the contractions is observed at 48 h after the poisoning with hydrogen peroxide in the case of the perfluorinated compounds $A_3$ and $A_4$ used at a concentration of 100 μM, and the hydrocarbon compounds $A_1$ and $A_2$, used at a concentration of 100 or 200 μM (table 1). While the other compounds protect the cells from breakdown, they do not permit recovery of the contractions.

The apoptosis state was then quantified, after lyzing the cells and centrifuging, by assaying the quantity of fragmented DNA in the supernatants using a "cell death detection ELISA" kit. After enzymic visualization, the optical densities are measured at 405 nm using a plate reader (FIG. 9).

The results clearly indicate that all the compounds tested, apart from the ionic derivative $B_1$, protect the cells from the apoptosis which is induced by adding hydrogen peroxide. At a concentration of 200 mM, the carboxylate derivative $B_1$ exhibits a very low artefactual apoptosis signal which is due, prior to cell lysis, to the release of DNA fragments into the culture medium after the cultured cells which have been treated with this nitrone have died.

TABLE 2

| Criteria for observing the contractile activity of the muscle fibers | |
|---|---|
| 0 | No muscle fibers having contractile activity in the culture well |
| 0/+ | One muscle fiber having weak and irregular contractile activity |
| + | One muscle fiber having regular contractile activity |
| ++ | 2 to 4 muscle fibers having contractile activity |
| +++ | More than 4 muscle fibers having contractile activity | c. Assessing the Antioxidant Activity on Fibroblast Cell Lines Suffering from a Severe Deficit of the Respiratory Chain Complex V: Using the MTT Test to Determine Cell Viability The tests are carried out on fibroblast cell lines which are characterized by a mutation of the NARP gene, which encodes a protein (subunit 6) of the V complex of the mitochondrial chain. These cells are characterized by an abnormal overproduction of the enzyme superoxide dismutase, suggesting that this genetic deficiency gives rise to an increase in the production of superoxide free radical. This over-production of superoxide free radical gives rise to a process in which apoptosis of the cells is accelerated (Geromel V., Kadhom N., Cebalos-Picot I., Ouari O., Polidori A., Munnich A., Rötig A., Rustin P. *Hum. Mol. Genet.* (2001) 10, 1221-1228).

TABLE 1

Measuring the contractile activity of nerve-muscle cell cultures 48 h after poisoning with 800 μM $H_2O_2$

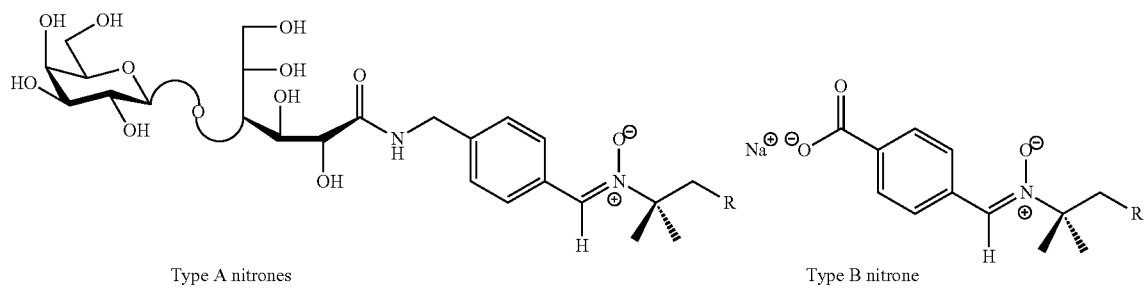

Type A nitrones | Type B nitrone

| | | | Contractile activity of the muscle fibers (number of wells) | | | | |
|---|---|---|---|---|---|---|---|
| Nitrones | R | [C] μM | 0 | + | ++ | +++ | % contractile inactivity |
| $A_1$ | $C_7H_{15}CONH$ | 100 | | | 2 | | 0 |
| | | 200 | | 3 | | | 0 |
| $A_2$ | $C_8H_{17}S$ | 100 | 3 | | | | 100 |
| | | 200 | 2 | | | | 100 |
| $A_3$ | $C_6F_{13}CH_2CH_2S$ | 100 | | | | 3 | 0 |
| | | 200 | 1 | 1 | | 1 | 33.3 |
| $A_4$ | $C_6F_{13}CH_2CH_2CONH$ | 100 | 1 | 2 | | | 33.3 |
| | | 200 | 3 | | | | 100 |
| $B_1$ | $C_8H_{17}S$ | 100 | cd[1] | | | | 100 |
| | | 200 | cd | | | | 100 |
| PBN | | 200 | cd | | | | 100 |
| DMPO | | 200 | cd | | | | 100 |
| Control | | | | | 1 | 1 | 0 |
| $H_2O_2$ Control | | | 3 | 1 | | | 75 |

[1] cell death

Fibroblast cultures were prepared from skin biopsies obtained from two individuals (controls) and a patient who was a carrier of the NARP mutation. The cells were cultured in RPMi 1640 medium (marketed by Life technologies SARL, Cergy Pontoise, France) to which glutamax (446 mg/l), 10% undialyzed fetal calf serum, 100 µg of streptomycin/ml, 100 IU of penicillin/ml, 200 µM uridine and 2.5 mM sodium pyruvate were added. For the cytotoxicity tests, the cells were seeded, at a density of 3000 cells per well, in Petri microplates at 37° C. and under 5% $CO_2$. In order to initiate the oxidative stress, the cell is subjected, after 24 hours, to a hypoglycemia by replacing the glucose with 10 mM galactose (selective medium marked sm in FIGS. 10a to 10f). After 24 hours, the cells were exposed, for 48 hours and 72 hours, to increasing concentrations of the different compounds to be tested in selective medium intended for respiratory cells (RPMi 1640 medium without glucose). For comparison purposes, all the studies were carried out on cells which were harvested after one and the same population doubling.

The antioxidant activity of the amphiphilic nitrones was assessed using the MTT test to measure their ability to protect the cells against apoptosis.

The MTT test is a colorimetric method which makes it possible to determine the number of viable cells in proliferation and cytotoxicity assays. The wells were incubated with 20 µl of a solution of MTT (5 mg/ml in PBS) at 37° C. for 1 hour. After that, 200 µl of isopropanol were added in order to extract the MTT formazan and the absorbance of each well was measured at 540 nm using an automated reading appliance.

The results which were obtained with the MTT colorimetric assays are illustrated by FIGS. 10a to 10f. In these figures, the compound $A_5$ is a type A nitrone in which R=OCONH $(CH_2)_5CH_3$ and the compound H corresponds to the following formula:

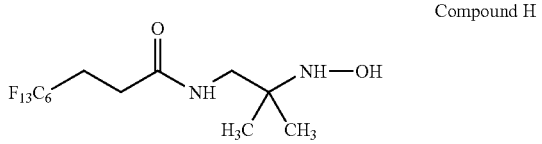

Compound H

This test demonstrates the ability of TA1PBN, at concentrations of 50 µM and above, to protect NARP cells from cell death due to apoptosis. These results provide good confirmation of the analyses which have previously been carried out on TA1PBN (Geromel V., Kadhom N., Cebalos-Picot I., Ouari O., Polidori A., Munnich A., Rötig A., Rustin P. *Hum. Mol. Genet.* (2001) 10, 1221-1228). The perfluorocarbon compound $B_1$ also appears to be effective at concentrations of 100 µM and above. It is to be noted that the perfluorocarbon compound $A_4$ and the hydrocarbon compounds $A_1$, $A_2$ and $A_5$ are not effective in this cell model. This defect in efficacy can be attributed to the fatty hydrocarbon chains lacking hydrophobicity. The chain length of the perfluorinated compound $A_4$ is less than that of the compound $A_3$. It is finally to be noted that, at $C_8F_{17}$, the perfluorinated chain of TA1PBN is longer than that of the compound $A_3$ ($C_6F_{13}$ chain). This may explain the difference in efficacy when treating NARP cells with these two amphiphilic nitrones. Tests on derivatives which are analagous to $A_3$ and which possess a $C_8F_{17}$ fluorinated chain are in progress. In conclusion, it appears that the degree of hydrophobicity of these nitrones appears to play a crucial role in their biological activity. The latter is probably determined by the ability of the nitrone to be transferred across the cytoplasmic membrane and, possibly, into the mitochondrial cavity.

II—Examples of Syntheses

1. Synthesizing an Amphiphilicmonocatenary Glycosylated Hydrocarbon Nitrone a. Synthesizing 4-methylbenzene sulfonate from 2-methyl-2-nitropropyl E3

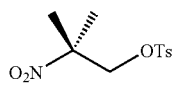

9.6 g of tosyl chloride (0.050 mol-1.2 equivs.) are dissolved in 30 ml of pyridine. 5 g of 2-methyl-2-nitropropanol (0.042 mol-1 equiv.) dissolved in 30 ml of dichloromethane are then added dropwise. The medium is maintained at 0° C. during the addition and then at room temperature for 48 hours. The reaction mixture is poured into 150 ml of ice water while stirring vigorously. The aqueous phase is extracted with 3 times 50 ml of dichloromethane. The organic phases are combined, washed with 3 times 75 ml of 3N HCl, then with 2 times 75 ml of brine, dried over $Na_2SO_4$ and finally evaporated under reduced pressure. Following recrystallization in an ethyl acetate/cyclohexane mixture, the compound E3 is obtained in the form of a light white powder (9.55 g-0.035 mol-83%). Front ratio: 0.35 (cyclohexane/ethyl acetate, 8:2). M.p.=74-75.5° C.

$^1$H NMR (250 MHz, $CDCl_3$): δ 7.76 (2H, d, J=8.5 Hz, H arom.), 7.37 (2H, d, J=8.5 Hz, H arom.), 4.27 (2H, s, $CH_2$—O), 2.46 (3H, s, $CH_3$ of the tosyl), 1.56 (6H, s, $CH_3$ of the tert-butyl)

$^{13}$C NMR (62.86 MHz, $CDCl_3$): δ 146.1 ($C^{IV}$ arom.), 132.6 ($C^{IV}$ arom.), 130.7 and 128.6 (CH arom.), 86.3 ($C^{IV}$), 73.2 ($CH_2$—O), 23.5 ($CH_3$ of the tert-butyl), 22.3 ($CH_3$ of the tosyl)

Infrared (KBr, $cm^{-1}$): $\nu_{(CH\ arom.)}$=3059 and 3005, $\nu_{(NO2)}$=1543 b. Synthesizing 1-octanesulfanyl-2-methyl-2-nitropropyl E7a

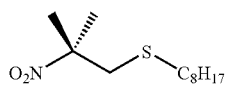

4.1 g of potassium tert-butoxide (0.039 mol-2 equivs.) are suspended in 30 ml of anhydrous DMF under an argon atmosphere. After stirring for 20 minutes, 6.4 ml of octanethiol (0.039 mol-2 equivs.), dissolved in 10 ml of DMF, are added dropwise using a dropping funnel. The medium progressively assumes a milky white appearance and, after 10 minutes, 5 g of E3 (0.0183 mol-1 equiv.), dissolved in 20 ml of DMF, are added slowly. The reaction mixture is brought to 50° C., under an argon flow, for 4 hours. The mixture is poured into 400 ml of ice brine and this mixture is then extracted with 5 times 50 ml of cyclohexane. The organic phase is washed with 2 times 100 ml of brine, dried-over $Na_2SO_4$ and evaporated under reduced pressure. Following purification by flash chromatography on silica gel (eluent: cyclohexane/dichloromethane, from 9:1 to 8:2), the compound E7a (4.4 g-0.0178 mol-97%) is obtained in the form of an oil. Rf: 0.65 (cyclohexane/ethyl acetate, 8:2).

$^1$H NMR (250 MHz, CDCl$_3$): δ 3.04 (2H, s, C$^{IV}$—CH$_2$—S), 2.52 (2H, t, J=7.25 Hz, CH$_2$—S), 1.64 (6H, s, CH$_3$ of the tert-butyl), 1.54 (2H, qt, J=7.25 Hz, CH$_2$—CH$_2$—S), 1.40 to 1.20 (10H, m, CH$_2$ of the chain), 0.87 (3H, t, J=7 Hz, CH$_3$ of the chain).

$^{13}$C NMR (62.86 MHz, CDCl$_3$): δ 87.4 (C$^{IV}$), 41.5 (C$^{IV}$—CH$_2$); 33.2 (CH$_2$—S), 30.8, 28.8, 28.1 and 27.7 (CH$_2$ of the chain), 24.4 (CH$_3$ of the tert-butyl), 21.6 (CH$_2$ of the chain), 13.1 (CH$_3$ of the chain).

Infrared (KBr, cm$^{-1}$): ν$_{(NO2)}$=1543 c. Synthesizing N-(1,1-dimethyl-2-octyl-sulfanyl-ethyl)hydroxylamine E7b

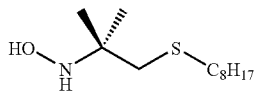

0.247 g of nitro compound E7a (1 mmol-0.25 equiv.) is dissolved in 6 ml of a THF/MeOH mixture (2:1) which has been previously degassed with argon. This solution is added, all at the same time, to Kagan's reagent (4 equivs.) under an inert atmosphere. The reaction, which is almost instantaneous, is followed by the appearance of a green/gray coloration (disappearance of the SmI$_2$ species in favor of the SmI$_3$ species). After 15 minutes of stirring, 20 ml of a 10% solution of Na$_2$S$_2$O$_3$ are added to the reaction medium. The THF is evaporated under reduced pressure. The aqueous phase is diluted 2 times and then extracted with 3 times 30 ml of ethyl acetate. The organic phase is washed with 2 times 30 ml of distilled water and then evaporated under reduced pressure. The purification by means of silica gel chromatography (eluent: cyclohexane/ethyl acetate, from 8:2 to 7:3) leads to the hydroxylamine E7b (164 mg-0.7 mmol-70%) in the form of a translucent oil.

50 mg of the starting compound E7a are also recovered and make it possible to determine a conversion rate of 88%.

$^1$H NMR (250 MHz, DMSO: δ 7.09 (1H, s, NH), 5.3 (1H, bs, OH), 2.63 (2H, s, C$^{IV}$—CH$_2$—S), 2.55 (2H, t, J=7.2 Hz, CH$_2$—S), 1.64 (6H, s, CH$_3$ of the tert-butyl), 1.54 (2H, qt, J=6.7 Hz and J=7.2 Hz, CH$_2$—CH$_2$—S), 1.40 to 1.20 (10H, m, CH$_2$ of the chain), 0.87 (3H, t, J=7 Hz, CH$_3$ of the chain)

$^{13}$C NMR (62.86 MHz, CDCl$_3$): δ 57.2 (C$^{IV}$), 40.8 (C$^{IV}$—CH$_2$), 33.2 (CH$_2$—S), 31.2, 29.4, 28.6 and 28.5 (CH$_2$ of the chain), 23.7 (CH$_3$ of the tert-butyl), 22.0 (CH$_2$ of the chain), 13.9 (CH$_3$ of the chain)

Infrared (KBr, cm$^{-1}$): ν$_{(NH)}$=3246 d. Synthesizing the Hydrocarbon Nitrone A2

0.5 g of glycosylated aldehyde (Ouari O., Chalier F., Pucci B., Tordo P., J. Chem. Soc. Perkin Trans 2 (1998), 2299) (0.615 mmol-1 equiv.) is dissolved, under an argon atmosphere, in 10 ml of anhydrous and degassed THF. 0.1 g of hydroxylamine E7b (0.430 mmol-0.7 equiv.), dissolved in 2 ml of THF, is added, as is a spatula tip of 4 Å molecular sieve. The reaction mixture is brought to 60° C., under argon and while being shielded from light. 50 mg of hydroxylamine (0.215 mmol-0.35 equiv.) and a spatula tip of 4 Å molecular sieve are added every second day. The progress of the reaction is assessed by TLC and, after 8 days and addition of 1.75 equivs. of hydroxylamine, the reaction medium is filtered through celite. After the solvents have been evaporated under reduced pressure, the crude reaction mixture is purified by flash chromatography through silica gel (eluent: ethyl acetate/cyclohexane, 7:3). An additional purification is carried out on LH-20 exclusion resin (eluent: methanol/dichloromethane, 1:1) and leads to the pure nitrone A2 (313 mg-0.304 mmol-50%) and to 116 mg of a fraction comprising the starting aldehyde (in a ratio of approximately ⅓ as determined by $^1$H NMR). M.p.=70° C. (decomp.). [α]$_D$=+17.8° (c, 1, CH$_2$Cl$_2$).

$^1$H NMR (250 MHz, CDCl$_3$): δ 8.24 (2H, d, J=8.1 Hz), 7.49 (1H, s, CH=N(O)), 7.25 (2H, d, J=8.1 Hz), 6.57 (1H, m, NH), 5.67 (1H, d, J=6.6 Hz, H-2), 5.60 (1H, dd, J=3.8 Hz and J=5.8 Hz, H-3), 5.37 (1H, d, J=3 Hz, H-4'), 5.18 (1H, dd, J=2.5 Hz and J=10.3 Hz, H-2'), 5.08 (1H, m, H-5), 4.98 (1H, dd, J=3.4 Hz and J=10.4 Hz, H-3'), 4.65 (1H, d, J=7.9 Hz, H-1'), 4.62 to 4.45 (2H, m, 1H-6a and H-7a), 4.42 to 4.30 (2H, m, H-4 and H-7b), 4.23 to 3.98 (3H, m, H-6b, H-6'a and H-6'b), 3.90 (1H, t, J=6.5 Hz), 3.00 (2H, s, C$^{IV}$—CH$_2$—S), 2.41 (2H, t, J=7.25 Hz, CH$_2$—S), 2.13, 2.05, 2.02, 2.01, 1.98, 1.95 (24H, 6s, CH$_3$—CO), 1.61 (6H, s, CH$_3$ of the tert-butyl), 1.43 (2H, m, CH$_2$—CH$_2$—S) 1.3 to 1.1 (10H, m, CH$_2$ of the chain), 0.82 (3H, t, J=6.6 Hz, CH$_3$ of the chain).

$^{13}$C NMR (62.86 MHz, CDCl$_3$): δ 170.4, 170.4, 170.0, 170.0, 169.9, 169.7, 169.7, 169.5, 169.2 (CH$_3$—CO), 167.1 (CO—NH), 139.8 (C$^{IV}$ arom.), 131.0 (CH=N(O)), 130.1 (C$^{IV}$ arom.), 129.2, 127.5 (CH arom.), 101.7 (CH-1'), 77.3 (CH-4), 73.4 (C$^{IV}$), 71.7 (CH-2), 70.9 (CH-5' and CH-3'), 69.7 (CH-5), 69.1 (CH-3), 68.9 (CH-2), 66.8 (CH-4'), 61.6, 60.9 (CH$_2$—OAc), 42.9 CH$_2$—NH), 42.4 (C$^{IV}$—CH$_2$—S), 33.3 (CH$_2$—S), 31.7, 29.9, 29.0, 29.0, 28.6 (CH$_2$ of the chain), 25.7 (CH$_3$ of the tert-butyl), 22.5 (CH$_2$ of the chain), 20.8, 20.7, 20.6, 20.6, 20.6, 20.5, 20.5, 20.4 (CH$_3$—CO), 14.0 (CH$_3$ of the chain).

MS FAB+ (1027.1 g.mol$^{-1}$): [M+H]$^+$=1027 (5%), [M+Na]$^+$=1049 (10%), [C$_{12}$H$_{25}$S]$^+$=201 (70%).

The deprotected product is obtained after deacetylating the sugars using the method of Zemplen:

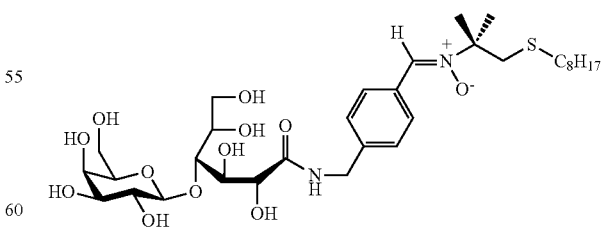

M.p.=115° C. (decomp.)
Rf: 0.52 (ethyl acetate/methanol/water, 7:2:1)
[α]$_D$=+17.2 (0.25c, 1, CH$_3$OH)
$^1$H NMR (250 MHz, CD$_3$OD): δ 8.28 (2H, d, J=8.25 Hz), 7.82 (1H, s, CH=N(O)), 7.42 (2H, d, J=8.25 Hz), 4.65 to 4.35

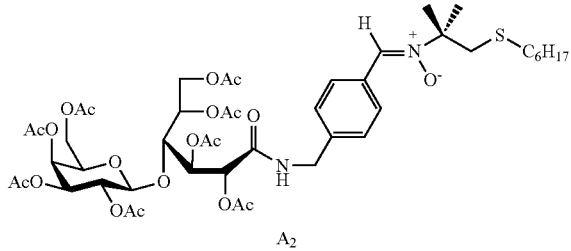

A2

(4H, m, CH$_2$—NH, H-1', H-2), 4.25 (1H, m, H-3), 4.00 to 3.35 (10H, m, H-4, H-5, CH$_2$—OH, H-4', H-5', H-3' and H-2'), 3.01 (2H, 2, CH$_2$—S), 2.43 (2H, t, J=7.3 Hz, CH$_2$—S), 1.61 (6H, singlet, CH$_3$ of the tert-butyl), 1.44 (2H, m, CH$_2$), 1.3 to 1.1 (10H, m, CH$_2$), 0.87 (3H, t, J-6.9 Hz)

$^{13}$C NMR (62.86 MHz, CD$_3$OD); δ 175.3 (CO—NH), 143.4 ($C^{IV}$ arom.), 136.0 (CH=N(O)), 131.1 (CH arom.), 130.6 ($C^{IV}$ arom.), 128.3 (CH arom.), 105.8 (CH-1'), 83.3 (CH-4), 77.2 (CH-5'), 74.8 ($C^{IV}$), 74.6 (CH-3' or CH-2'), 74.1 (CH-2), 73.2 (CH-5), 72.8 (CH-3' or CH-2'), 72.5 (CH-3), 70.4 (CH-4'), 63.8, 62.7 (CH$_2$—OH), 43.5, 43.0 (CH$_2$—NH and CH$_2$—S), 34.2 (CH$_2$—S), 32.9, 31.0, 30.3, 30.2, 29.7 (CH$_2$), 26.0 (CH$_3$ of the tert-butyl), 23.7 (CH$_2$), 14.4 (CH$_3$)

UV (MeOH, nm): $\lambda_{max}$=299

MS FAB+ (690.8 g.mol$^{-1}$): No [M+H]$^+$, [M+Na]$^+$=713 (2.5%), [M+K]$^+$=729 (1.5%), [C$_{12}$H$_{25}$S]$^+$=201 (65%)

MS FAB$^-$ (690.8 g.mol$^{-1}$): [M-H]$^-$=689 (very weak)

HPLC (Microsorb C18-21.4 mm/250 mm): tr=11.4 min

Gradient of 70 MeOH-30 H$_2$O to 85 MeOH-15 H$_2$O from t=0 to t=5 min

Isocratic 85 MeOH-15 H$_2$O from t=5 min

Flow rate 0.6 ml/min

2. Synthesizing the Fluorocarbon Nitrone A$_4$ a. Synthesizing 1-azido-2-methyl-2-nitro-propane

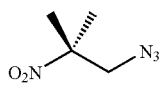

6 g of the compound E3 (0.0218 mol-1 equiv.) and 2.3 g of sodium azide (0.0353 mol-1.6 equivs.) are reacted in 20 ml of DMF under ultrasonic activation (large probe-1 sec pulse/2 sec rest-90% amplitude) while cooling the medium with an ice bath. After 3 hours of sonication, and the complete disappearance of the starting compound, the reaction medium is taken up in 50 ml of dichloromethane and then poured, while stirring vigorously, onto 300 ml of ice brine. The aqueous phase is extracted with 2 times 50 ml of dichloromethane, after which the organic phases are combined, washed with 2 times 75 ml of brine, dried over Na$_2$SO$_4$ and evaporated under reduced pressure. After residual traces of DMF have been eliminated at 50° C. under the vacuum produced by a vane pump, the final compound (2.66 g-0.0185 mol-85%) is obtained in the form of a very fluid translucent yellow oil.

$^1$H NMR (250 MHz, CDCl$_3$): δ 3.74 (2H, s, CH$_2$—N$_3$), 1.60 (6H, s, CH$_3$ of the tert-butyl)

$^{13}$C NMR (62.86 MHz, CDCl$_3$): δ 86.7 ($C^{IV}$), 58.3 (CH$_2$—N$_3$), 23.9 (CH$_3$ of the tert-butyl)

Infrared (KBr, cm$^{-1}$): $\nu_{(N3)}$=2111, $\nu_{(NO2)}$=1546 b. Synthesizing 2-methyl-2-nitropropylamine E4

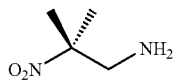

4.08 g of azide (0.0283 mol-1 equiv.) are dissolved, under a flow of nitrogen, in 10 ml of anhydrous and degassed THF. 11.3 g of triphenyl-phosphine (0.0431 mol-1.50 equivs.), dissolved in 30 ml of THF, are added dropwise to the azido compound. A powerful evolution of gas takes place. After 2 hours of stirring at room temperature under a nitrogen atmosphere, 20 ml of an aqueous solution of 2N sodium hydroxide are added and the medium is left to stand for 24 hours. The THF is evaporated under reduced pressure, and the aqueous phase is acidified to pH 1 by adding 20 ml of 3N HCl and then extracted with 2 times 30 ml of ethyl acetate. The aqueous phase is then rendered alkaline by adding solid sodium hydroxide to a pH of 10, after which it is extracted with 3 times 30 ml of dichloromethane. The organic phase is washed with 2 times 30 ml of water, dried over Na$_2$SO$_4$ and evaporated under reduced pressure. The amine E4 (2.90 g-0.0245 mol-87%) is obtained in the form of a yellow oil.

$^1$H NMR (250 MHz, CDCl$_3$): δ 3.07 (2H, s, CH$_2$—NH$_2$), 1.57 (6H, s, CH$_3$ of the tert-butyl)

$^{13}$C NMR (62.86 MHz, CDCl$_3$): δ 9.4 ($C^{IV}$), 51.1 (CH$_2$—NH$_2$), 23.6 (CH$_3$ of the tert-butyl)

In view of its instability, we synthesized the corresponding ammonium hydrochloride for the purpose of characterizing and storing it:

The amine is taken up in 60 ml of ether into which gaseous HCl is bubbled for 10 minutes. The medium is placed at –20° C. for 2 hours and then filtered under reduced pressure. After the traces of solvent have been eliminated using a vane pump, the ammonium hydrochloride of E4 (3.75 g-0.0243 mol-quantitative yield) is obtained in the form of a white powder.

$^1$H NMR (250 MHz, D$_2$O): δ 3.62 (2$\underline{H}$, s, C$\underline{H}_2$NH$_3^+$Cl$^-$), 1.72 (6H, s, CH$_3$ of the tert-butyl)

$^{13}$C NMR (62.86 MHz, D$_2$O): δ 87.0 ($C^{IV}$), 46.9 (CH$_2$—NH$_3^+$Cl$^-$), 24.8 (CH$_3$ of the tert-butyl)

Infrared (KBr, cm$^{-1}$): $\nu_{(NO2)}$=1541 c. Synthesizing 4,4,5,5,6,6,7,7,8,8,9,9,9-tridecafluorononanoyl (2-methyl-2-nitropropyl)amide E5a

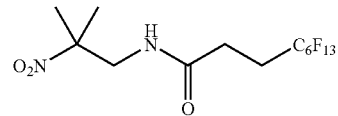

Under a nitrogen atmosphere, 2.47 g of DCC (0.0120 mol-1.2 equivs.) and a spatula tip of HOBt are dissolved in 10 ml of anhydrous dichloromethane. 1.41 g of the amine E4 (0.012 mol-1.2 equivs.), dissolved in 10 ml of dichloromethane, are added to the medium. The solution is degassed for several minutes after which 3.86 g of fluoric acid (0.0098 mol-1 equiv.) dissolved in 30 ml of ethyl acetate are added all at once. After 36 hours of stirring, the reaction medium is filtered and the organic phase is washed respectively with 2 times 50 ml of 1N HCl and 2 times 50 ml of brine, after which it is dried over Na$_2$SO$_4$ and evaporated under reduced pressure. Purification by means of silica gel chromatography (eluent: cyclohexane/ethyl acetate, 8:2 to 7:3) leads to the compound E5a (4.4 g-8.94 mmol-91%) in the form of a white powder. M.p.=87.3-88.8° C. Rf: 0.37 (cyclohexane/ethyl acetate, 8:2).

$^1$H NMR (250 MHz, CDCl$_3$): δ 6.11 (1H, massive, NH), 3.76 (2H, d, CH$^{IV}$—CH$_2$—NH, J=6.75 Hz), 2.55 to 2.42 (4H, massive, CH$_2$—CH$_2$—Rf), 1.58 (6H, massive, CH$_3$ of the tert-butyl)

$^{13}$C NMR (62.86 MHz, CDCl$_3$): δ 170.5 (CO), 88.7 (C$^{IV}$), 46.1 (CH$_2$—NH—), 24.1 (CH$_3$ of the tert-butyl)

$^{19}$F NMR (235 MHz, CDCl$_3$): δ −81.1 (CF$_3$, singlet), −114.8 (CF$_2$—CH$_2$, singlet), −122.1, −123.1, and −123.8 (CF$_2$, singlet), −126.4 (CF$_2$—CF$_3$)

Infrared (KBr, cm$^{-1}$): ν$_{(NH)}$=3280, ν$_{(C=O)}$=1664, ν$_{(NO2)}$=1547, ν$_{(CF2)}$=1246 d. 4,4,5,5,6,6,7,7,8,8,9,9,9-Tridecafluorononanoyl (2-hydroxyamino-2-methylpropyl)amide E5b

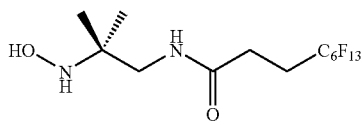

The experimental procedure is identical to that used for the first hydroxylamine E7b. 1.71 g of nitro compound E7a (3.5 mmol-0.25 equiv.), dissolved in 20 ml of THF/MeOH mixture, are added to 140 ml of Kagan's reagent.

Following treatment and purification by means of silica gel chromatography (eluent: ethyl acetate/methanol, 10:0 to 9.5:0.5), the hydroxylamine E7b (0.82 g-1.7 mmol-49%) is obtained in the form of a white powder.

0.56 g of the starting compound E7a are also recovered and make it possible to determine a rate of conversion of 72%. M.p.=110.5-112.3° C. Rf: 0.58 (ethyl acetate/methanol, 95:5).

$^1$H NMR (250 MHz, DMSO): δ 7.79 (1H, t, J=6.0 Hz, NH)), 6.89 (1H, s, NH), 5.23 (1H, bs, OH), 3.05 (2H, d, J=6.0 Hz, CH$_2$—NH), 2.48 (4H, m, CH$_2$—CH$_2$—Rf), 0.86 (6H, s, CH$_3$ of the tert-butyl)

$^{13}$C NMR (62.86 MHz, DMSO): δ 169.7 (CO), 56.9 (C$^{IV}$), 44.7 (C$^{IV}$—CH$_2$); 22.4 (CH$_3$ of the tert-butyl)

$^{19}$F NMR (235 MHz, DMSO): δ −80.0 (CF$_3$, singlet), −113.4 (CF$_2$—CH$_2$, singlet), −121.5, −122.5 and −123.0 (CF$_2$, singlet), −125.6 (CF$_2$—CF$_3$, singlet e. Synthesizing the Fluorocarbon Nitrone A4

The experimental procedure is identical to that used for the first nitrone.

0.61 g of aldehyde (0.75 mmol-1 equiv.) are reacted with the hydroxylamine E7b (0.26 g-0.7 equiv.) in 15 ml of THF. The reaction is stopped after 10 days of stirring and the addition of 0.35 g of additional hydroxylamine (0.732 mmol-0.98 equiv.).

The purifications are carried out by means of flash chromatography on silica gel (eluent: ethyl acetate/methanol, 10:0 to 95:5) and by means of exclusion chromatography on LH-20 resin (eluent: methanol/dichloromethane, 1:1). The nitrone A$_4$ is obtained as a pure compound (0.564 g-0.443 mmol-60%) in the form of a white foam. The starting aldehyde (115 mg-0.142 mmol) is also recovered, making it possible to determine a rate of conversion of 73%. M.p.=95° C. (decomp.).

$^1$H NMR (250 MHz, CDCl$_3$): δ 8.21 (2H, d, J=8.1 Hz), 7.49 (1H, s, CH=N(O)), 7.31 (2H, d, J=8.1 Hz), 6.95 (1H, t, J=6 Hz, NH), 6.76 (1H, t, J=6 Hz, NH), 5.45 to 3.80 (15H), 3.69 (2H, d, J=6.0 Hz, C$^{IV}$—CH$_2$—NH), 2.70 to 2.35 (4H, m, CH$_2$—CH$_2$—Rf), 2.17, 2.16, 2.08, 2.07, 2.06, 2.05, 2.04, 1.98 (24H, 8s, CH$_3$—CO), 1.60 (6H, s, CH$_3$ of the tert-butyl)

$^{13}$C NMR (62.86 MHz, CDCl$_3$): δ 170.6 (CO—NH+CH$_3$—CO), 170.4, 170.2, 170.1, 170.0, 169.8, 169.7, 169.3 (CH$_3$CO), 167.3 (CO—NH), 140.6 (C$^{IV}$ arom.), 131.5 (CH=N(O)), 129.8 (C$^{IV}$ arom.), 129.4, 127.7 (CH arom.), 101.9 (CH-1'), 77.5 (CH-4), 73.4 (C$^{IV}$), 71.7 (CH-2), 71.0 (CH-5' and CH-3'), 70.0 (CH-5), 69.3 (CH-3), 69.1 (CH-2), 66.9 (CH-4'), 61.8, 60.9 (CH$_2$—OAc), 47.3, 43.1 (CH$_2$—NH), 27.0 ( ), 24.9 (CH$_3$ of the tert-butyl), 20.9, 20.8, 20.7, 20.7, 20.6, 20.5 (CH$_3$—CO)

$^{19}$F NMR (235 MHz, CDCl$_3$): δ −81.1 (CF$_3$, s), −115.0 (CF$_2$—CH$_2$, s), −122.3, −123.2, −123.9 (CF$_2$, s), −126.5 (CF$_2$—CF$_3$, s)

MS FAB$^+$ (1272.0 g.mol$^{-1}$): [M+H]=1273 (1.5%), [M+Na]=1295 (3.5%)

The deprotected product is obtained after deacetylating the sugars using the method of Zemplen:

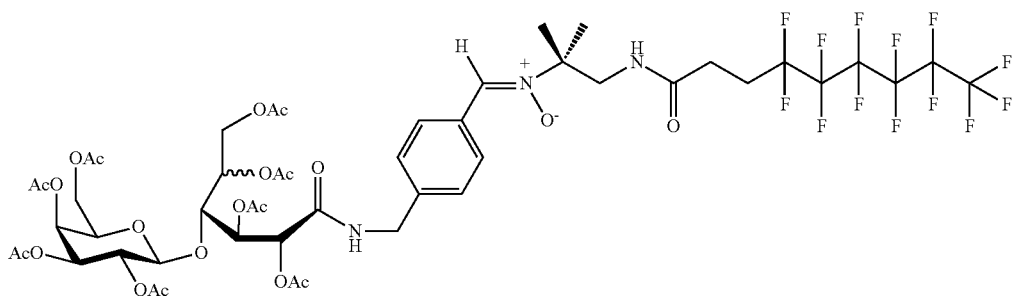

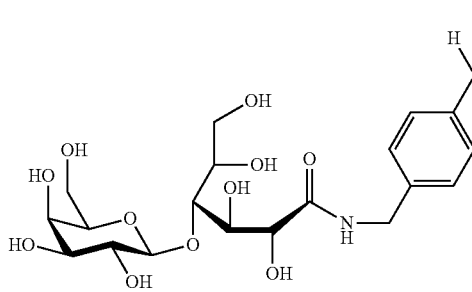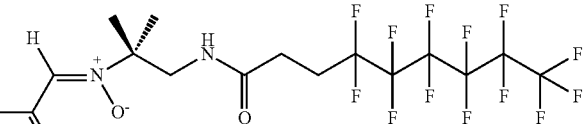

M.p.=150° C. (decomp.)

[α]$_D$=+14.4 (0.25c, 1, CH$_3$OH)

UV (MeOH, nm): λ$_{max}$=299

Rf: 0.47 (ethyl acetate/methanol/water, 7:2:1)

$^1$H NMR (250 MHz, CD$_3$OD): δ 8.33 (2H, d, J=8.4 Hz), 7.86 (1H, s, CH=N(O)), 7.47 (2H, d, J=8.5 Hz), 4.65 to 4.45 (4H, m, CH$_2$—NH, H-1', H-2), 4.3 (1H, m, H-3), 4.05 to 3.87 (2H, m, H-4 and H-5), 3.87 to 3.66 (7H, m, CH$_2$—OH, H-4' and CH$_2$—NH), 3.66 to 3.45 (3H, m, H-5', H-3' and H-2'), 2.55 to 2.40 (4H, m, CH$_2$—CH$_2$—Rf), 1.59 (6H, singlet, CH$_3$ of the tert-butyl)

$^{13}$C NMR (62.86 MHz, CD$_3$OD): δ 174.0, 171.9 (CO—NH), 142.1, (C$^{IV}$ arom.), 134.6 (CH=N(O)), 129.7 (CH arom.), 129.2, (C$^{IV}$ arom.), 126.9 (CH arom.), 104.4 (CH-1'), 82.0 (CH-4), 75.8 (CH-5'), 73.5 (C$^{IV}$), 73.4 (CH-3'or CH-2'), 72.7 (CH-2), 71.8 (CH-5), 71.4 (CH-3' or CH-2'), 71.2 (CH-3), 69.0 (CH-4'), 62.4 (CH$_2$-6), 61.3 (CH$_2$-6'), 46.3 (C$^{IV}$—CH$_2$—NH), 42.1 (C$^{IV}$ arom.-CH$_2$—NH), 26.0 (CH$_2$—CH$_2$—Rf), 23.3 (CH$_3$ of the tert-butyl)

$^{19}$F NMR (235 MHz, CD$_3$OD): δ –82.1 (CF$_3$, s), –115.3 (CF$_2$—CH$_2$, s), –122.6, –123.6, –124.3 (CF$_2$, s), –127.0 (CF$_2$—CF$_3$, s)

MS FAB$^+$ (935.7 g.mol$^{-1}$): [C$_{13}$H$_{13}$F$_{13}$NO]$^+$=446 1%), [C$_9$H$_4$F$_{13}$O]$^+$=375 (8%)

MS FAB$^-$ (35.7 g.mol$^{-1}$: [M–H]=934 (very weak)

Preparative column (Microsorb C18-21.4 mm/250 mm): tr=9.800

Gradient of 70 MeOH-30 H$_2$O to 80 MeOH-20 H$_2$O from t=0 to t=5 min

Gradient of 80 MeOH-20 H$_2$O to 82 MeOH-18 H$_2$O from t=5 to t=8 min

Isocratic, 82 MeOH-18 H$_2$O, from t=8 min onwards

Flow rate, 0.8 ml/min

3. Synthesizing the Ionic Hydrocarbon Nitrone B$_1$ a. Synthesizing [4-(1,3-dioxolan)-2-yl-benzyl]trimethylammonium iodide

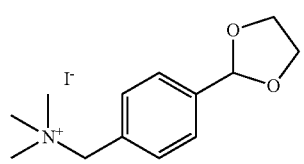

1.25 g of amine E15 (7 mmol-1 equiv.) are dissolved in 4 ml of DMF in a sealed tube. 2.58 g of tributylamine (14 mmol-2 equivs.) are then added all at once while stirring. The medium is cooled down to 0° C. and 5.2 g of methyl iodide (35 mmol-5 equivs.) are added slowly to it. The sealed tube is closed and the stirring is continued at room temperature for 20 hours. The crude reaction mixture is taken up in AcOEt and the resulting precipitate is filtered off, taken up in ether and then filtered once again. The ammonium compound (1.7 g-4.9 mmol-70%) is obtained in the form of a white powder.

$^1$H NMR (250 MHz, DMSO-d$_6$): δ 7.59 (4H, s, H arom.), 5.80 (H, s, H of the acetal), 4.61 (2H, s, CH$_2$—NH), 4.2 to 3.9 (4H, AA'BB', CH$_2$—O), 3.06 (9H, s, CH$_3$—N)

$^{13}$C NMR (62.86 MHz, DMSO-d$_6$): δ 140.6 (C$^{IV}$ arom.), 133.3 (CH arom.), 129.6 (C$^{IV}$ arom.), 127.5 (CH arom.), 102.7 (CH acetal), 67.6 (CH$_2$—N), 65.4 (CH$_2$—O), 52.2 (CH$_3$—N)

Percentage analysis (Cl3H20NO2I, 0.83 H2O), calculated C, 41.69; H, 4.60; N, 4.42. found C, 41.69; H, 4.58; N, 4.31.

b. Synthesizing (4-formylbenzyl)trimethylammonium iodide E26

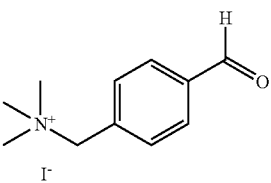

0.38 g of the dioxolane ammonium (1.08 mmol-1 equiv.) are dissolved in 10 ml of acetic acid/water mixture, 1:1. After 12 hours of stirring, the reaction medium is evaporated under vacuum and the traces of solvent are eliminated using a vane pump. The compound E26 (0.34 g-1.08 mmol-quantitative yield) is obtained in the form of a dark brown powder.

$^1$H NMR (250 MHz, DMSO-d$_6$): δ 10.12 (1H, s, CHO), 8.06 (2H, d, J=8 Hz, H arom.), 7.80 (2H, d, J=8 Hz, H arom.), 4.69 (2H, s, CH$_2$—NH), 3.09 (9H, s, CH$_3$—N)

$^{13}$C NMR (62.86 MHz, DMSO-d$_6$): δ 193.4 (CHO), 137.6, 134.8 (C$^{IV}$ arom.), 134.1, 130.2 (CH arom.), 62.2 (CH$_2$N), 52.6 (CH$_3$N)

c. Synthesizing the Ionic Fluorocarbon Nitrone B2

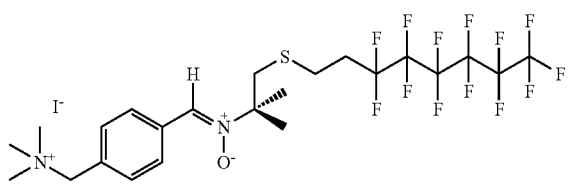

0.25 g of compound E26 (0.82 mmol-1 equiv.) and 0.48 g of hydroxylamine E7b (1.02 mmol-1.25 equivs.) are dissolved in 5 ml of pyridine which has been degassed with argon. The reaction medium is brought to 80° C., in the dark and under an argon atmosphere, for 42 hours. The reaction mixture is then evaporated under reduced pressure and the traces of pyridine are eliminated using a vane pump. The nitrone is obtained in the form of a white powder (0.35 g-0.47 mmol-57%) after two consecutive crystallizations in an MeOH/ether mixture. M.p.=171-173.

$^1$H NMR (250 MHz, CD$_3$OD): δ 8.54 (2H, d, J=8.4 Hz, H arom.), 8.03 (1H, s, CH=N(O)), 7.71 (2H, d, J=8.4 Hz, H arom.), 4.65 (2H, s, CH$_2$—N), 3.18 (11H, s, CH$_3$—N+C$^{IV}$—CH2—S), 2.7 (2H, m, CH$_2$—S), 2.45 (2H, m, CH$_2$—CH$_2$—Rf), 1.71 (6H, s, CH$_3$ of the tert-butyl)

$^{13}$C NMR (62.86 MHz, CD$_3$OD): δ 133.3 (C$^{IV}$ arom.), 132.8 (CH=N(O)), 132.7 (CH arom.), 129.8, (C$^{IV}$ arom.), 129.7 (CH arom.), 73.9 (C$^{IV}$), 68.5 (CH$_2$—N), 51.9, 51.9, 51.8 (CH$_3$—N), 41.3 (CH$_2$—S), 31.9 (CH$_2$—CH$_2$—Rf), 24.6 (CH3 tert-butyl), 23.0 (CH$_2$—CH$_2$—Rf)

$^{19}$F NMR (235 MHz, CD$_3$OD): δ −82.3 (CF$_3$, singlet), −115.2 (CF$_2$—CH$_2$, singlet), −112.9, −123.9, −124.3 (CF$_2$, singlet), −127.3 (CF$_2$—CF$_3$, singlet)

UV (MeOH, nm): λ$_{max}$=304 nm

HR MS FAB$^+$ (754.4 g.mol$^{-1}$): theoretical m/z: 755.0838 for C$_{23}$H$_{29}$F$_{13}$IN$_2$OS ([M+H]$^+$)

Observed m/z: 755.0851

MS FAB$^+$ (754.4 g.mol$^{-1}$): [2M+H]$^+$=1510, [2M−I]$^+$=1381 (5%), [M+H]$^+$=755 (2.5%), [M−I]$^+$=627 (100%), [C$_{12}$H$_{12}$F$_{13}$S]$^+$=435 (100%)

4. Synthesizing the Bicatenary Hydrocarbon Nitrone C1 a. Synthesizing 3-heptadecylcarbamoyloxy-2-methyl-2-nitropropyl heptadecyl carbamate E9a

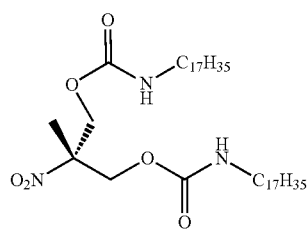

6.31 g of stearic acid (0.022 mol-3 equivs.) are suspended in 50 ml of anhydrous toluene under an argon atmosphere. 2.47 g of triethylamine (0.024 mol-3.3 equivs.) and 6.71 g of diphenyl-phosphoryl azide (0.024 mol-3.3 equivs.) are added and the medium is brought to 60° C. After 2 hours of stirring, 1 g of 2-nitro-2-methyl-1,3-propanediol (0.0074 mol-1 equiv.) and a spatula tip of DABCO are added in suspension and the stirring is continued for 12 hours. The crude reaction mixture is diluted with 100 ml of ethyl acetate, washed with 3 times 50 ml of 1N HCl and 3 times with 50 ml of saturated NaHCO$_3$, and finally washed with 2 times 50 ml of brine. The organic phase is dried over Na$_2$SO$_4$ and evaporated under reduced pressure. After 3 consecutive crystallizations, the compound E9a (2.02 g-2.89 mmol-40%) is obtained in the form of a white powder. M.p.: 75-76.2° C.

Rf: 0.42 (cyclohexane/ethyl acetate, 8:2)

$^1$H NMR (250 MHz, CDCl$_3$): δ4.77 (2H, m, NH), 4.45 (2H, AB system, CH$_2$—O), 3.15 (2H, q, J=9.8 Hz, CH$_2$—NH), 1.59 (3H, s, CH$_3$ of the tert-butyl), 1.47 (2H, m, CH$_2$—CH$_2$—NH), 1.24 (55H, m, CH$_2$ of the chain), 0.87 (3H, t, CH$_3$ of the chain)

$^{13}$C NMR (62.86 MHz, CDCl$_3$): δ 155.1 (CO), 88.1 (C$^{IV}$), 65.1 (CH$_2$—O), 41.3 (CH$_2$—NH), 31.9, 29.8, 29.7, 29.6, 29.5, 29.4, 29.3 (CH$_2$ of the chain), 26.7 (CH$_3$ of the tert-butyl), 22.7, 18.5 (CH$_2$ of the chain), 14.1 (CH$_3$ of the chain)

Infrared (KBr, cm$^{-1}$): ν$_{(NH)}$-3392, ν$_{(CO)}$-1720 and 1703, ν$_{(NO2)}$=1549 b. Synthesizing heptadecylcarbamoyl 3-hepta-decyl-carbamoyloxy-2-hydroxylamino-2-methylpropyl ester E9b

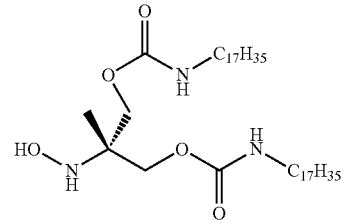

The experimental procedure is identical to that used for synthesizing the compounds E5b and E7b.

1.39 g of the nitro compound E9a (2.0 mmol-0.25 equiv.), dissolved in 20 ml of THF/MeOH mixture, are added to 80 ml of Kagan's reagent.

After treatment and purification by silica gel chromatography (eluent: dichloromethane/ethyl acetate, from 10:0 to 5:5), the hydroxylamine E9b (0.8 g-1.17 mmol-60%) is obtained in the form of a white powder.

0.24 g of the starting compound E9a is also recovered and makes it possible to obtain a rate of conversion of 71%. M.p.=80-81.6° C.

Rf: 0.51 (cyclohexane/ethyl acetate, 5:5)

$^1$H NMR (250 MHz, CDCl$_3$): δ 4.83 (2H, t, J=NH), 4.45 (4H, AB system, CH$_2$—O), 3.17 (4H, q, J=9.8 Hz, CH$_2$—NH), 1.49 (2H, m, CH$_2$—CH$_2$—NH), 1.25 (55H, m, CH$_2$ of the chain), 1.07 (3H, s, CH$_3$ of the tert-butyl), 0.88 (3H, t, CH$_3$ of the chain)

$^{13}$C NMR (62.86 MHz, CDCl$_3$): δ 156.7 (CO), 88.1 (C$^{IV}$), 64.7 (CH$_2$—O), 41.2 (CH$_2$—NH), 31.9, 29.8, 29.7, 29.6, 29.5, 29.4, 29.3 (CH$_2$ of the chain), 26.8 (CH$_3$ of the tert-butyl), 22.7, 16.8 (CH$_2$ of the chain), 14.1 (CH$_3$ of the chain)

c. Synthesizing the Biantennary Hydrocarbon Nitrone C1

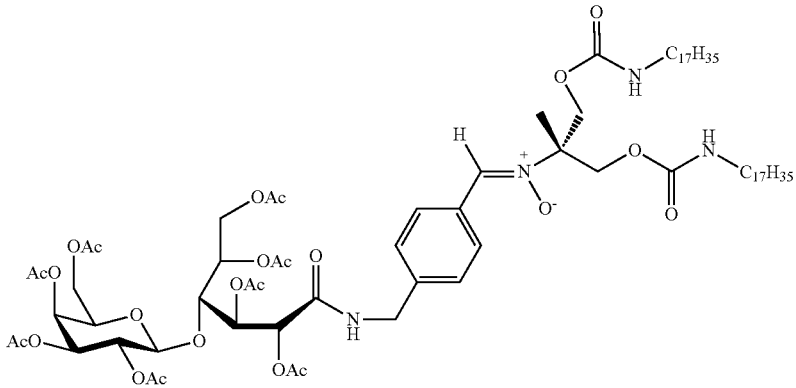

0.5 g of aldehyde E20 (0.616 mmol-1 equiv.) is dissolved, in the presence of 4 Å molecular sieve and 0.3 g of hydroxylamine E9b (0.44 mmol-0.71 equiv.), in 6 ml of anhydrous and degassed THF. 1.2 ml of glacial acetic acid are added and the medium is warmed to 50° C. under argon and sheltered from light.

0.2 g of hydroxylamine (0.29 mmol-0.47 equiv.) is added after 48 and 96 hours and the reaction medium is filtered through celite at the end of 5 days of reaction.

The purifications by means of flash chromatography on silica gel (eluent: ethyl acetate/dichloromethane, from 7:3 to 8:2) and by means of exclusion chromatography on Sephadex LH-20 resin (eluent: ethanol/dichloromethane, 1:1) make it possible to obtain the type C nitrone (0.58 g-0.392 mmol-63%) almost free from traces of aldehyde and in the form of a white powder. 80 mg of pure aldehyde are also recovered, making it possible to determine a rate of conversion of 76%. $[\alpha]_D = +16.9°$ (c, 1, $CHCl_3$) at 20° C.

Rf: 0.37 (ethyl acetate/dichloromethane, 8:2)

$^1H$ NMR (250 MHz, $CDCl_3$): δ 8.28 (2H, d, J=8.1 Hz, H arom.), 7.45 (1H, s, CH=N(O)), 7.31 (2H, d, J=8.5 Hz, H arom.), 6.65 (1H, t, J=5.8 Hz, NH amide), 5.75 to 5.55 (2H, m, H-2 and H-3), 5.35 (1H, d, J=3 Hz), 5.25 to 4.80 (5H, m, H-2', H-5, H-3' and NH urethane), 4.70 to 4.25 (9H, m, H-1', H-6a and H-7a, H-4, H-7b and $CH_2$—O—CO—NH), 4.20 to 3.80 (4H, m, H-6b, H-6'a, H-6'b and H-5'), 3.14 (4H, dd, J=6.7 Hz, $CH_2$—NH—CO—O), 2.16, 2.15, 2.09, 2.05, 2.04, 1.98, 1.92 (24H, 8s, $CH_3$—CO), 1.60 (3H, s, $CH_3$ of the tert-butyl), 1.55 to 1.10 (60H, m, $CH_2$ of the chain), 0.87 (6H, t, J=6.4 Hz, $CH_3$ of the chain)

$^{13}C$ NMR (250 MHz, $CDCl_3$): δ 170.6, 170.3, 170.2, 170.0, 169.9, 169.8, 169.4, ($CH_3$—$\underline{C}O$), 167.3 (CO—NH), 155.7 (O—CO—NH), 140.3 ($C^{IV}$ arom.), 132.4 (CH=N (O)), 130.0 ($C^{IV}$ or CH arom.), 129.6 ($C^{IV}$ or CH arom.), 127.8 (CH arom.), 101.9 (CH-1'), 77.4 (CH-4), 75.1 ($C^{IV}$), 71.7 (CH-2), 71.1 (CH-5' and CH-3'), 69.9 (CH-5), 69.3 (CH-3), 69.1 (CH-2), 66.9 (CH-4'), 65.5 ($CH_2$—O—CO—NH), 61.8 and 61.0 ($CH_2$—OAc), 43.2 ($CH_2$—NH), 41.3 ($CH_2$—NH—CO—O), 32.0, 29.9, 29.8, 29.7, 29.7, 29.6, 29.4, 29.3 ($CH_2$ of the chain), 26.8 ($CH_3$ of the tert-butyl), 22.8 ($CH_2$ of the chain), 20.9, 20.9, 20.8, 20.7, 20.7, 20.6 ($CH_3$—CO), 14.2 ($CH_3$ end of chain)

MS $FAB^+$ (1477.8 g.$mol^{-1}$): [M+H]=1478 (16%), [M+Na]= 1500 (6%).

The deprotected product is obtained after deacetylating the sugars using the method of Zemplen:

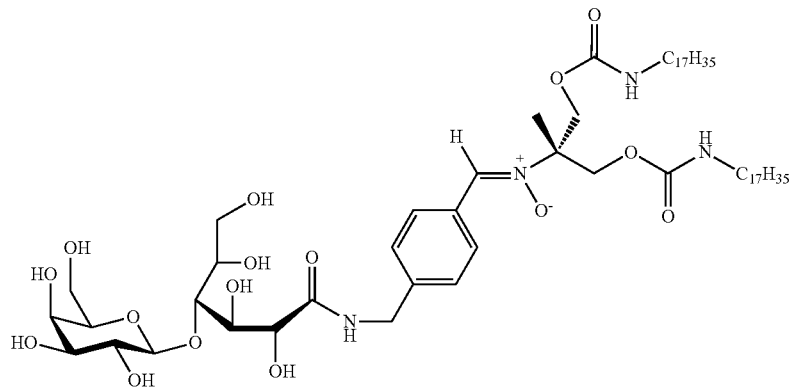

The nitrone $C_1$ is purified by flash chromatography on silica gel (eluent: chloroform/methanol/water, 8:2:0.1) and then by size exclusion chromatography on Sephadex LH-20 (eluent: dichloromethane/methanol, 7:3).

$[\alpha]_D = +7.6°$ (0.25c, 1, $CHCl_3$)

Rf: 0.28 (chloroform/methanol/water, 8:2:0.1)

M.p.=190° C. (decomp.)

$^1$H NMR (250 MHz, DMSO-d6): δ 8.28 (2H, d, J=8.2 Hz, H arom.), 8.07 (1H, t, J=6.3 Hz, NH amide), 7.72 (1H, s, CH=N(O)), 7.35 (2H, d, J=8.3 Hz, H arom.), 7.08 (2H, m, NH urethane), 4.60 to 4.00 (9H, m, $CH_2$—NH, $CH_2$—O—CO—NH, H-1', H-2 and H-3), 3.78 (2H, m, H-4 and H-5), 3.70 to 3.40 (8H, m, $CH_2$—OH, H-2', H-3', H-4' and H-5'), 2.94 (4H, m, $CH_2$—NH—CO—O), 1.54 (3H, s, $CH_3$ of the tert-butyl), 1.45 to 1.10 (60H, m, $CH_2$), 0.87 (6H, t, J=6.6 Hz, $CH_3$)

$^{13}$C NMR (62.86 MHz, DMSO-d6): δ 173.0 (CO—NH), 156.1 (O—CO—NH), 142.3 ($C^{IV}$ arom.), 132.1 (CH=N(O)), 130.0 ($C^{IV}$ arom.), 129.1 (CH arom.), 127.2 (CH arom.), 105.1 (CH-1'), 83.4 (CH-4), 76.2 (CH-5'), 74.9 ($C^{IV}$), 73.7 (CH-3' or CH-2'), 72.6 (CH-2), 71.9 (CH-5), 71.6 (CH-3' or CH-2'), 71.1 (CH-3), 68.7 (CH-4'), 65.1 ($CH_2$—O—CO—NH), 62.8, 61.1 ($CH_2$-6 and $CH_2$-6'), 42.2 ($CH_2$—NH), 40.7 ($CH_2$—NH—CO—O), 31.8, 29.8, 29.6, 29.2 ($CH_2$ of the chain), 26.7 ($CH_3$ of the tert-butyl), 22.6 ($CH_2$ of the chain), 14.4 ($CH_3$ of the chain)

MS FAB$^+$ (1140.77 g.mol$^{-1}$): [M+Na]=1164, [M+H]=1142

III—Measuring the Hydrophobicity of the Molecules of the Invention

One of the objectives of the invention is to modulate the HLB of free radical traps in order to promote transmembrane passage and transport in vivo.

From this perspective, it was important to determine the partition coefficient P of these compounds.

Thus, during a study of the efficacy of the action of different hypnotics in dependence on their hydrophobicity, Hansch and his coworkers (Hansch, C.; Steward, A. R.; Anderson, S. M.; Bentley, D. *J. Med. Chem.* 11, 1 (1968)). established the following relationship:

$$\log 1/C = -k(\log P)^2 + k'(\log P) + k''$$

C: the molar concentration producing a standard biological response k, k' and k": constants determined by the method of least squares.

Thus, the more hydrophobic a compound is, the more the value log P will be greater than 0 and the more the interactions with the lipid phase will be increased.

We have determined the partition coefficients of these nitrones by means of reverse phase high performance liquid chromatography (Lambert, W. J. *J. Chromtogr.* 656, 469 (1993); Dorsey, J. G.; Kahaledi, M. G. *J. Chromtogr.* 656, 485 (1993)).

Thomas has also used this chromatographic approach for determining the hydrophobicity of cyclic spin traps derived from PBN (Fevig, T. L.; Bowen, S. M.; Janowick, D. A.; Jones, B. K.; Munson, H. R.; Ohlweiler, D. F.; Thomas, C. E. *J. Med. Chem.* 39, 4988 (1996)). The estimation of the octanol/water partition coefficient by means of reverse phase HPLC ($K_{OW}$) is highly dependent on the retention times of the compounds and, consequently, on the capacity coefficient k'. It can be expressed by the following relationship:

$$\log K_{OW} = a \log k' + b$$

In which a and b are empirical constants which characterize the solvent system.

Experimentally, k' is determined by the following formula for different methanol/water eluent mixtures.

$$k' = (t_R - t_0)/t_0$$

in which $t_R$ represents the retention time of the sample and $t_0$ the elution time of the mobile phase.

It is then necessary to extrapolate, by linear regression, the value of k' for a phase composed of 100% water in order to obtain the value $k_W$.

We have proceeded in this manner in the case of the type A compounds derived from lactobionic acid. We have also, with a view to comparing and validating our model, determined the hydrophobicity of PBN and of TA1PBN.

Table 3 summarizes the mean retention times obtained from a minimum of 3 values established on a minimum of 2 different days.

The linear regression of the k values, obtained in dependence on the mobile phases employed, makes it possible to obtain a straight-line equation of the type:

$$y = ax + b$$

in which y represents log k' and a represents log k'$_W$ and x represents the methanol fraction of the eluent.

TABLE 3

Using HPLC to determine the values of log k'

| | Mobile phase (MeOH/H$_2$O) | | | | | | | |
|---|---|---|---|---|---|---|---|---|
| | 60/40 | | 70/30 | | 80/20 | | 90/10 | |
| Nitrones | 225–235 bar | | 200–220 bar | | 175–195 bar | | 140–160 bar | |
| (C in mg/ml) | $t_R$ | log k' | $t_R$ | log k' | $t_R$ | log k' | $t_R$ | log k' |
| MEOH | 3.98 | | 3.97 | | 3.94 | | 3.89 | |
| PBN (0.64 mg/ml) | 7.98 | 0.0019 | 6.09 | −0.2711 | 5.07 | −0.5405 | 4.47 | −0.8203 |
| TA1PBN (0.26 mg/ml) | — | — | 28.92 | 0.7985 | 8.46 | 0.0593 | 4.85 | −0.6057 |
| A2 (0.52 mg/ml) | — | — | 22.43 | 0.6676 | 9.06 | 0.1140 | 5.31 | −0.4344 |
| A3 (0.52 mg/ml) | — | — | 29.28 | 0.8047 | 9.04 | 0.1119 | 4.87 | −0.5967 |
| A1 (0.48 mg/ml) | 9.98 | 0.1776 | 6.14 | −0.2624 | 4.76 | −0.6840 | — | — |

TABLE 3-continued

Using HPLC to determine the values of log k'

| Nitrones | Mobile phase (MeOH/H₂O) | | | | | | | |
|---|---|---|---|---|---|---|---|---|
| | 60/40 225–235 bar | | 70/30 200–220 bar | | 80/20 175–195 bar | | 90/10 140–160 bar | |
| (C in mg/ml) | $t_R$ | log k' | $t_R$ | log k' | $t_R$ | log k' | $t_R$ | log k' |
| A4 (0.57 mg/ml) | 41.41 | 0.9731 | 12.64 | 0.3394 | 6.12 | −0.2562 | — | — |
| A5 (0.52 mg/ml) | 8.21 | 0.0264 | 5.51 | −0.4143 | 4.49 | −0.8524 | — | — |

We have proceeded in the same manner in the case of the other 4 derivatives, and the results are summarized in the following table (table 4).

TABLE 4

Using HPLC to determine the values of log k'w

| | a | R² | log k'w |
|---|---|---|---|
| PBN | −2.7366 | 0.9999 | 1.6447 |
| TA1PBN | −7.0209 | 0.9991 | 5.7008 |
| $A_2$ | −5.5098 | 1 | 4.5235 |
| $A_3$ | −7.0079 | 1 | 5.7129 |
| $A_1$ | −4.3082 | 0.9998 | 2.7595 |
| $A_4$ | −6.1468 | 0.9997 | 4.6549 |
| $A_5$ | −4.3942 | 1 | 2.6635 |

Out of a concern for clarity, we have transferred the log k'$_w$ values of the different nitrones to a histogram (FIG. 11).

The results obtained enable us to make several comments and conclusions:

1—In the case of the compounds having hydrocarbon chains, the values obtained are in agreement with our expectations. The magnitude of the hydrophobicity is in direct proportion to the number of carbon atoms in the chain. On the other hand, the role played by the nature of the chain junctions in the value of log k' is not insignificant, with an amide or urethane bond being by nature more polar than a thioether junction. The following order of increasing hydrophobicity is therefore obtained:

2—In the case of the fluorinated compounds, compound $A_3$ exhibits a greater affinity for lipid media than does compound $A_4$, an observation which appears to be in agreement with their respective CMC values. However, compounds $A_3$ and $A_4$ possess log k'$_w$ values which are close to each other whereas their CMC values vary by more than a factor of two. This stems from the nature of the fluorinated chains, which exhibit unusual surfactant properties. It is therefore necessary to make a clear separation between the concept of surfactant activity and the concept of hydrophobicity. The following order of increasing hydrophobicity is therefore obtained:

3—The value of log k'$_w$ for PBN is appreciably lower than that of any of the synthesized compounds. According to Hansch's theory, we can deduce from this that the compounds have better transmembrane penetration and therefore a superior activity in trapping free radicals.

4—The value of log k'$_w$ for TA1PBN is roughly identical to that of the compound $A_3$.

The invention claimed is:

1. A compound corresponding to the formula (I):

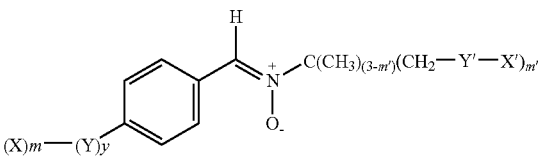

in which:

X represents a group selected from: glucose, fructose, mannose, galactose, ribose, maltose, glucosamine, sucrose and lactobionamide, a poly(ethylene oxide) chain consisting of from 30 to 100 ethylene oxide units, a group selected from,

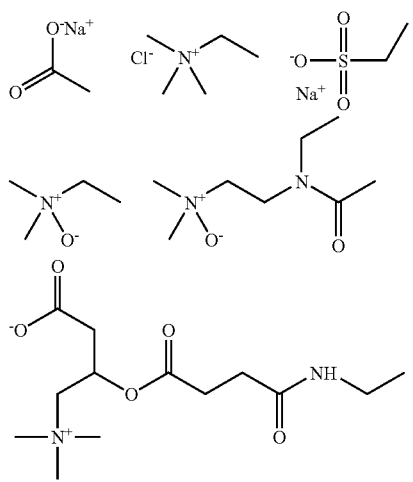

m represents an integer equal to 1, 2 or 3;

Y represents a spacer arm which is intended to link the aromatic nucleus to the hydrophilic X substituents; and Y is selected from

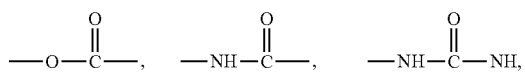

-continued

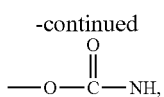

—O—, —S—, —NH—, and $C_1$-$C_6$ hydrocarbon chains which are optionally interrupted by one or more of the following groups:

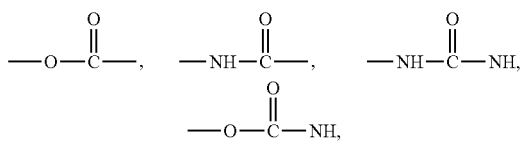

—O—, —S—, —NH—;
y represents an integer equal to 0 or to 1;
Y' represents a group selected from

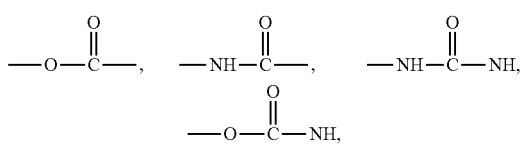

—O—, —S—;
m' is an integer selected from 1 and 2;
X' represents a hydrogen atom or a $C_4$-$C_{14}$ alkyl chain which is optionally substituted by one or more fluorine atoms.

2. The compound as claimed in claim 1, wherein X represents a group selected from: glucose, lactose, manose, galactose, ribose, maltose, glucosamine, sucrose and lactobionamide.

3. A compound as claimed in claim 1, wherein X represents a group selected from poly(ethylene oxide) chains consisting of from 50 to 60 units.

4. A compound as claimed in claim 1, wherein X represents a group selected from

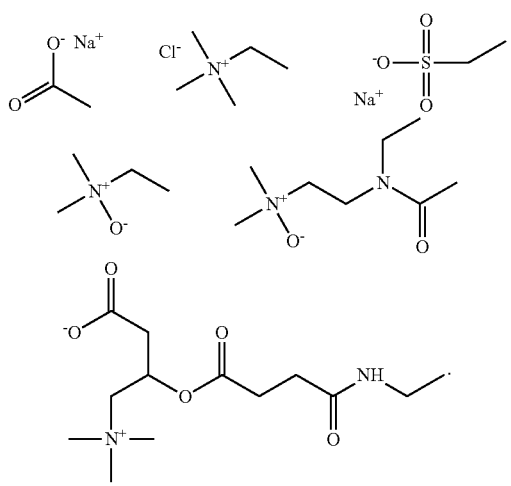

5. A compound as claimed in claim 1, wherein at least one of the following conditions is satisfied:

X represents a group selected from: lacto-bionamide,
m represents 1;
m' represents 1 or 2;
X' is selected from the groups octyl, decyl, dodecyl and $CF_3(CF_2)_rCH_2CH_2$—, where $8 \geq r \geq 6$.

6. A process for preparing a compound corresponding to the formula (I) as claimed in claim 1 wherein an aldehyde corresponding to the formula (II) is reacted with a hydroxylamine corresponding to the formula (III) in accordance with scheme 2 below:

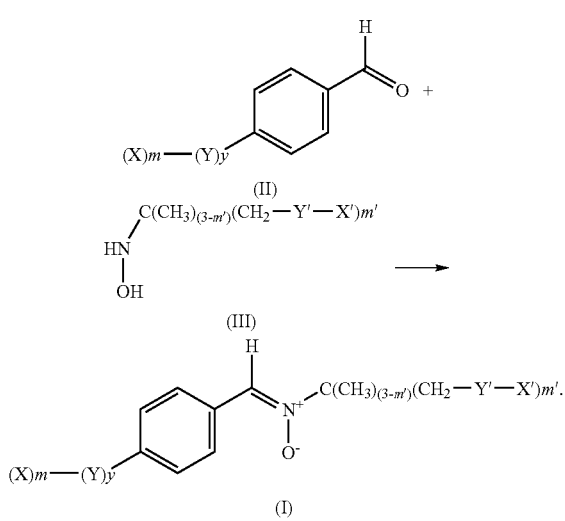

7. The process as claimed in claim 6, wherein the compound of the formula (III) is prepared in accordance with a process which is described in scheme 3:

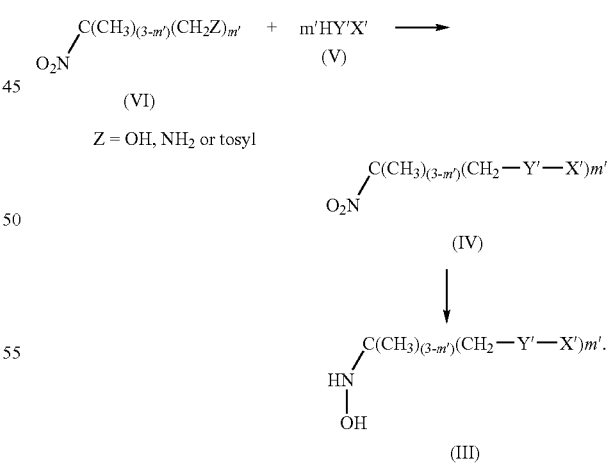

8. A pharmaceutical composition comprising at least one compound corresponding to the formula (I) as claimed in claim 1 in a pharmaceutically acceptable excipient.

9. A cosmetic composition, comprising at least one compound corresponding to the formula (I) as claimed in claim 1 in a cosmetically acceptable excipient.

10. A method of capturing free radicals comprising the step of reacting a free radical with the compound as claimed in claim 1.
11. A compound as claimed in claim 1, wherein X represents a group selected from: glucosamine, sucrose and lactobionamide.
12. The compound as claimed in claim 1, wherein Y represents a group selected from:
—NH$_2$—CH$_2$—,
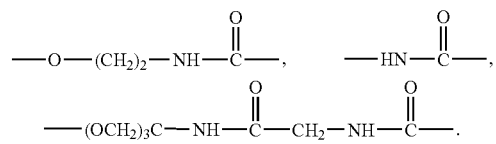

UNITED STATES PATENT AND TRADEMARK OFFICE
CERTIFICATE OF CORRECTION

PATENT NO.        : 7,655,251 B2                                                        Page 1 of 1
APPLICATION NO.   : 10/533982
DATED             : February 2, 2010
INVENTOR(S)       : Durand et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 984 days.

Column 10,
Line 25,

" 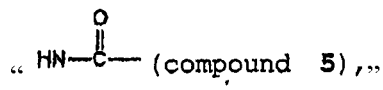 (compound 5),"

should read

-- Y' = 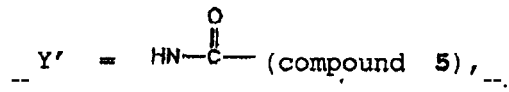 (compound 5), --.

Column 37,
Lines 5, 13, 16, 25, 27, each occurrence, "NH" should read -- NH— --.

Signed and Sealed this
Twenty-eighth Day of December, 2010

David J. Kappos
*Director of the United States Patent and Trademark Office*